US008809368B2

(12) United States Patent
Hua et al.

(10) Patent No.: US 8,809,368 B2
(45) Date of Patent: Aug. 19, 2014

(54) COMPOUNDS AFFECTING GAP JUNCTION ACTIVITY

(75) Inventors: Duy H. Hua, Manhattan, KS (US); Dolores J. Takemoto, Manhattan, KS (US); Thu Nguyen, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 1024 days.

(21) Appl. No.: 12/259,437

(22) Filed: Oct. 28, 2008

(65) Prior Publication Data

US 2009/0143425 A1 Jun. 4, 2009

Related U.S. Application Data

(63) Continuation-in-part of application No. PCT/US2007/067652, filed on Apr. 27, 2007.

(60) Provisional application No. 60/910,593, filed on Apr. 6, 2007, provisional application No. 60/745,909, filed on Apr. 28, 2006.

(51) Int. Cl.
*A61K 31/47* (2006.01)
*C07D 215/18* (2006.01)
*C07D 215/38* (2006.01)
*C07D 401/06* (2006.01)
*C07D 215/40* (2006.01)

(52) U.S. Cl.
CPC .................................. *C07D 215/40* (2013.01)
USPC ............................. 514/311; 546/171; 546/178

(58) Field of Classification Search
None
See application file for complete search history.

(56) References Cited

U.S. PATENT DOCUMENTS

| 4,376,511 A | 3/1983 | Franklin, Jr. |
| 4,431,807 A * | 2/1984 | Strube et al. .................. 546/171 |
| 4,617,394 A | 10/1986 | Blumberg et al. |
| 4,980,360 A | 12/1990 | Nodiff |
| 5,134,168 A | 7/1992 | Bitonti et al. |
| 6,180,675 B1 | 1/2001 | Widdowson et al. |
| 6,376,511 B2 | 4/2002 | McChesney et al. |
| 6,479,660 B1 | 11/2002 | Ugwuegbulam et al. |
| 7,145,014 B2 | 12/2006 | Bell et al. |
| 2006/0172956 A1 | 8/2006 | Bonner, Jr. et al. |

FOREIGN PATENT DOCUMENTS

WO    WO 2007/127930    11/2007

OTHER PUBLICATIONS

LaMontagne et al., Antimalarials. 14. 5-(Aryloxy)-4-methylprimaquine analogs. A highly effective series of blood and tissue schizonticidal agents, 25(9) J. Med. Chem. 1094-7 (1982) (CAS Abstract Only; see STN search report).*

Johnson et al., Synthesis and antileishmanial activity of 6-methoxy-4-methyl-N-[6-(substituted-1-piperazinyl)hexyl]-8-quinolinamines and related compounds, 26(2) J. Med. Chem.185-94 (1983) (CAS Abstract Only; See STN search report).*
Paul et al., 5-Aryloxy-6-methoxy-8-aminoquinolines as potential prophylacic antimalarials, 65(10) J. Pharma. Sci. 1527-30 (1976) (CAS Abstract).*
Johnson et al., Synthesis and antileishmanial activity of 6-methoxy-4-methyl-N-[6-(substituted-1-piperazinyl)hexyl]-8-quinolinamines and related compounds, 26(2) J. Med. Chem. 185-94 (1983) (CAS Abstract).*
Lauer et al., Some Derivatives of 8-Aminoquinoline, 68 J. Am. Chem. Soc. 1546-8 (1946).*
Xu et al., Synthesis and antimalarial activities of some 5-substituted phenoxy-8-aminoquinolines, 17(4) Yaoxue Tongbao 249-50 (1982).*
Chen et al., Synthesis of analogs of 4-methyl-5-(p-fluorophenoxy)primaquine as a tissue schizonticide of malaria parasite, 21(9) Yaoxue Xuebao 698-701 (1986).*
Acevedo et al. (1995) "Liarozole Potentiates the Cancer Chemopreventive Activity of and the Up-Regulation of Gap Junction Communication and Connexin43 Expression by Retinoic Acid and Beta-Carotene in 10T1/2 Cells," *Carcinogenesis* 16(9):2215-2222.
American Cancer Society (2006) "Cancer Facts and Figures," www.cancer.org.
Aminova et al. (Feb. 4, 2005) "Prosurvival and Prodeath Effects of Hypoxia-Inducible Factor-1—Stabilization in a Murine Hippocampal Cell Line," *J. Biol. Chem.* 280(5):3996-4003.
Ammerpohl et al. (Web Release Sep. 21, 2004) "HDACi Phenylbutyrate Increases Bystander Killing of HSV-tk Transfected Glioma Cells," *Biochem. Biophys. Res. Commun.* 324(1):8-14.
Beyer et al. (Oct. 1, 1990) "Connexin Family of Gap Junction Proteins," *J. Membr. Biol.* 116:187-194.
Bhimani et al. (1993) "Inhibition of Oxidative Stress in HeLa Cells by Chemoprotective Agents," *Cancer Res.* 53(19):4528-4533.
Borch et al. (1971) "The Cyanohydridoborate Anion as a Selective Reducing Agent," *J. Am. Chem. Soc.* 93:2897-2904.
Borman (Sep. 21, 2006) "Antimalarial Agent Hits Novel Enzyme," *Chemical and Engineering News* p. 17.
Boyle et al. (2006) "Hypoxia: Targeting the Tumor," *Anti-Cancer Agents in Med. Chem.* 6(4):281-286.
Britz-Cunningham et al. (May 18,1995) "Mutations of the *Connexin43* Gap-Junction Gene in Patients with Heart Malformations and Defects of Laterality," *N. Engl. J. Med.* 332(20):1323-1329.
Brueckner et al. (1998) "First-Time-In-Humans Safety and Pharmacokinetics of WR 238605, A New Antimalarial," *Am. J. Trop. Med. Hyg.* 58(5):645-649.

(Continued)

*Primary Examiner* — Janet L Andres
*Assistant Examiner* — Timothy R Rozof
(74) *Attorney, Agent, or Firm* — Lathrop & Gage LLP

(57) ABSTRACT

This invention relates to novel quinoline compounds which affect gap junction activity. Also provided are methods of using such compounds and compositions containing the compounds to treat gap junction disorders.

17 Claims, 21 Drawing Sheets

(56) References Cited

OTHER PUBLICATIONS

Bruzzone et al. (1996) "Connections with Connexins: The Molecular Basis of Direct Intercellular Signaling," *Eur. J. Biochem.* 238(1):1-27.
Butskus et al. (1961) "The Problem of Cyanothylation of Aromatic Amines," *Zhurnal Obshchei Khimii* 31:764-767.
Chiang et al. (May 2006) "Malaria: Therapy, Genes and Vaccines," *Curr. Mol. Med.* 6(3):309-326.
Clark et al. (2006) "Phase I-II Prospective Dose-Escalating Trial of Lycopene in Patients with Biochemical Relapse of Prostate Cancer After Definitive Local Therapy," *Urology* 67(6):1257-1261.
Cnubben et al. (2005) "Metabolism of ATP-Binding Cassette Drug Transporter Inhibitors: Complicating Factor for Multidrug Resistance," *Exp. Opin. Drug. Metab. Toxicol.* 1(2):219-232.
Contreras et al. (Web Release Sep. 30, 2004) "Role of Connexin-Based Gap Junctional Channels and Hemichannels in Ischemia-Induced Cell Death in Nervous Tissue," *Brain Res. Rev.* 47:290-303.
Cruikshank et al. (Aug. 17, 2004) "Potent Block of Cx36 and Cx50 Gap Junction Channels by Mefloquine," *Proc. Nat. Acad. Sci. USA* 101(33):12364-12369.
Cusato et al. (Jul. 23, 2003) "Gap Junctions Mediate Bystander Cell Death in Developing Retina," *J. Neurosci.* 23(16):6413-6422.
Dade et al. (Apr. 2001) "Synthesis of 2-Substituted Trifluoromethylquinolines for the Evaluation of Leishmanicidal Activity," *Chem. Pharm. Bull.* 49(4):480-483.
Das et al. (Web Release Jun. 30, 2008) "Protection of Retinal Cells from Ischemia by a Novel Gap Junction Inhibitor," *Biochem. Biophys. Res. Commun.* 373(4):504-508.
Das et al. (2006) "PKCγ Phosphorylates Connexin50 n Serine-430," A Presentation at the 2006 ARVO Annual Meeting, Apr. 30-May 4, Fort Lauderdale, Florida, E-Abstract No. 4089-B599.
DeGraw et al. (1977) "Potential Histidine Decarboxylase Inhibitors. 1. α- and β(Substitutes Histidine Analogs," *J. Med. Chem.* 20(12):1671-1674.
de Pina-Benabou et al. (2005) "Blockade of Gap Junctions in Vivo Provides Neuroprotection After Perinatal Global lschemia," *Stroke* 36:2232-2237.
Dubina et al. (2002) "Connexin 43, but not Connexin 32, is Mutated at Advanced Stages of Human Sporadic Colon Cancer," *Oncogene* 21(32):4992-4996.
Easson et al. (1931) "Amidines of Pharmacological Interest," *J. Chem. Soc.* :2991-3001.
Eghbali et al. (Dec. 1991) "Involvement of Gap Junctions in Tumorigenesis: Transfection of Tumor Cells with Connexin 32 cDNA Retards Growth in vivo," *Proc. Nat. Acad. Sci. USA* 88(23):10701-10705.
Farahani et al. (Web Release Apr. 21, 2005) "Alterations in Metabolism and Gap Junction Expression May Determine the Role of Astrocytes as 'Good Samaritans' or Executioners," *GLIA* 50:351-361.
Fingl et al. (1975) "General Principles," In; *The Pharmacological Basis of Therapeutics*, Ch.1,Macmillen Publishing Co., Inc.; New York, NY pp. 1-46.
Fleishman et al. (Feb. 2006) "Transmembrane Protein Structures Without X-Rays," *Trends Biochem. Sci.* 31(2):106-113.
Foley et al. (1998) "Quinoline Antimalearials: Mechanisms of Action and Resistance and Prospects for New Agents," *Pharmacol. Ther.* 79(1):55-87.
Foote et al. (Mar. 9, 1998) "The Pattern of Disulfide Linkages in the Extracellular Loop Regions of Connexin 32 Suggests a Model for the Docking Interface of Gap Junctions," *J. Cell Biol.* 140(5):1187-1197.
Gakhar et al. (Web Release Jan. 12, 2009) "Antitumor Effect of Substituted Quinolines in Breast Cancer Cells," *Drug. Dev. Res.* 69(8):526-534.
Gakhar et al. (2007) "Antitumor Effect of Primaquine Compounds in Breast Cancer Cells," Poster, Presented at the American Association for Cancer Research (AACR) Annual Meeting on Apr. 15th, 2007, Los Angeles, CA, Abstract #444.

Giepmans, B.N. (2004) "Gap Junctions and Connexin-Interacting Proteins," *Cardiovasc. Res.* 62(2):233-245.
Goldberg et al. (1994) "A Connexin 43 Antisense Vector Reduces the Ability of Normal Cells to Inhibit the Foci Formation of Transformed Cells," *Mol. Carcinog.* 11(2):106-114.
Goodsell et al. (1990) "Automated Docking of Substrates to Proteins by Simulated Annealing," *Prot. Struct. Funct. Genet.* 8:195-202.
Guo et al. (2006) "Hypoxia-Mimetic Agents Desferrioxamine and Cobalt Chloride Induce Leukemic Cell Apoptosis Through Different Hypoxia-Inducible Factor-1 a Independent Mechanisms," *Apoptosis* 11(1):67-77.
Hara et al. (Web Release Jul. 25, 2006) "A New Model of Retinal Photoreceptor Cell Degeneration Induced by a Chemical Hypoxia-Mimicking Agent, Cobalt Chloride," *Brain Res.* 1109:192-200.
Holder et al. (Aug. 1, 1993) "Gap Junction Function and Cancer," *Cancer Res.* 53(15):3475-3485.
Hong et al. (Web Release Dec. 8, 2006) "Combining the Rapid MTT Formazan Exocytosis Assay and the MC65 Protection Assay Led to the Discovery of Carbazole Analogs as Small Molecule Inhibitors of αβ Oligomer-Induced Cytotoxicity," *Brain Res.* 1130:223-234.
Huang et al. (2001) "Connexin 43 (9cx43) Enhances Chemotherapy-Induced Apoptosis in Human Glioblastoma Cells," *Int. J. Cancer* 92(1):130-138.
International Search Report and Written Opinion, Corresponding to International Application No. PCT/US07/67652, Mailed Jul. 28, 2008.
Jemal et al. (2007) "Cancer Statistics," *CA Cancer J. Clin.* 57(1):43-66.
Jones, R.G. (Dec. 1949) "Synthesis of Some Amines and Amino Acids Containing the Pyrazole Nucleus," *J. Am. Chem. Soc.* 71:3994-4000.
Kaji et all. (Jan. 1973) "The Synthetic Reactions of Alipathic Nitro Compounds. VII. The Synthesis of α-Amino Acids from the Nitroacetic Ester," *Bull. Chem. Soc. Japan* 46:337-338.
Kalkanidis et al. (2002) "Novel Phenothiazine Antimalarials: Synthesis, Antimalarial Activity, and Inhibition of the Formation of β-haematin," *Biochem. Pharmacol* 63:833-842.
Kamphuis et al. (Oct. 5, 2007) "Ischemic Preconditioning Alters the Pattern of Gene Expression Changes in Response to Full Retinal lschemia," *Mol. Vis.* 13:1892-1901.
Kawase et al. (2003) "New Multidrug Resistance Reversal Agents," *Curr. Drug Targets* 4(1):31-43.
Klenke et al. (Web Release Sep. 18, 2001) "Synthesis and Biological Evaluation of S-Triazine Substituted Polyamines as Potential New Anti-Trypanosomal Drugs," *J. Med. Chem.* 44(21):3440-3452.
LaMontagne et al. (1982) "Antimalarials 13. 5-Alkoxy Analogues of 4-Methylprimaquine," *J. Med. Chem.* 25(8):964-968.
LaMontagne, M.P. (1982) "14. 5-(Aryloxy)-4-Methylprimaquine Analogues. A Highly Effective Series of Blood and Tissue Schizonticidal Agents," *J. Med. Chem.* 25(9):1094-1097.
LaMontagne et al. (1989) "Antimalarials 16. Synthesis of 2-Substituted Analogs of 8-[(4-amino-1-methylbutyl)amino]-6-methoxy-4-methyl-5-[3-(trifluoromethyl)phenoxy]-quinoline as Candidate Antimalarials," *J. Med. Chem.* 32(8):1728-1732.
Lanzilli et al. (2006) "Resceratrol Down-Regulates the Growth and Telomerase Activity of Breast Cancer Cells in Vitro," *Int. J. Oncol* 28:641-648.
Lauer et al. (Aug. 1946) "Some Derivatives of 8-Aminoquinoline," *J. Am. Chem. Soc.* 68:1546-1548.
Leker et al. (2002) "Cerebral Ischemia and Trauma-Different Etiologies Yet Similar Mechanisms: Neuroprotective Opportunities," *Brain Res. Rev.* 39:55-73.
Levitt et al. (1999) "Tyrosine Kinase Inhibitors in Preclinical Development," *Invest New Drugs* 17:213-226.
Lin et al. (Apr. 8, 2005) "Oxidative Activation of Protein Kinase Cγ Through the C1 Domain. Effects on Gap Junctions," *J. Biol. Chem.* 280(14):13682-13693.
Lin et al. (Oct. 1998) "Gap-Junction-Mediated Propagation and Amplification of Cell Injury," *Nat. Neurosci.* 1(6):494-500.
Lin et al. (Web Release Aug. 17, 2007) "Protection from Ataxia-Linked Apoptosis by Gap Junction Inhibitors," *Biochem. Biophys. Res. Commun.* 362(4):982-987.

(56) References Cited

OTHER PUBLICATIONS

Livny et al. (2002) "Lycopene Inhibits Proliferation and Enhances Gap-Junction Communication of KB-1 Human Oral Tumor Cells," *J. Nutr.* 132(12):3754-3759.
Loewenstein, W.R. (1979) "Junction Intercellular Communication and the Control of Growth," *Biochim. Biophys. Acta* 560(1):1-65.
Loewenstein et al. (Mar. 16, 1966) "Intercellular Communication and the Control of Tissue Growth: Lack of Communication Between Cancer Cells," *Nature* 209(5029):1248-1249.
Loewenstein, W. R. (Oct. 1981) "Junctional Intracellular Communication: the Cell-to-Cell Membrane Channel," *Physiol. Rev.* 61(4):829-913.
Luker et al. (1996) "Kinetic Analysis of Plasmepsins I and II Aspartic Proteases of the *Plasmodium falciparum* Digestive Vacuole," *Mol. Biochem. Parasitol* 79:71-78.
Maezawa et al. (2006) "A Novel Tricyclic Pyrone Compound Ameliorates Cell Death Associated with Intracellular Amyloid-β Oligomeric Complexes," *J. Neurochem.* 98:57-67.
Makowski et al. (Aug. 1, 1977) "Gap Junction Structures. II. Analysis of the X-ray Diffraction Data," *J. Cell. Biol.* 74(2):629-645.
Martin et al. (2004) "Incorporation of Connexins into Plasma Membranes and Gap Junctions," *Cardiovasc. Res.* 62(2):378-387.
Matayoshi et al. (Feb. 23, 1990) "Novel Fluorogenic Substrates for Assaying Retroviral Proteases by Resonance Energy Transfer," *Science* 247:954-958.
McElvain et al. (Aug. 1942) "The Preparation of Orthoesters," *J. Am. Chem. Soc.* 64:1825-1827.
McNab, H. (1987) "Synthesis of pyrrol[1,2-c]imidazol-5-one, pyrrolo[1,2-a]o,odazol-5-one, and pyrrolo[1,2-b]pyrazol-6-one (Three Isomeric Azapyrrolizinones) by Pyrolysis of Meldrum's Acid Derivatives," J. Chem. Soc. Perkin Trans. 1: Org. Bio-Org. Chem. 3:653-656.
Morris et al. (1996) "Distributed Automated Docking of Flexible Ligands to Proteins: Parallel Applications of Autodock 2.4," *J. Computer-Aided Mol. Design* 10:293-304.
Morris et al. (1998) "Automated Docking Using Lamarckian Genetic Algorithm and an Empirical Binding Free Energy Function," *J. Comp. Chem.* 19(14):1639-1662.
Musil et al. (Aug. 18, 2000) "Regulation of Connexin Degradation as a Mechanism to Increase Gap Junction Assembly and Function," *J. Biol. Chem.* 275(33):25207-25215.
Na et al. (2000) "Restoration of Gap Junctional Intercellular Communication by Caffeic Acid Phenethyl Ester (CAPE) in a Ras-Transformed Rat Liver Epithelial Cell Line," *Cancer Lett.* 157(1):31-38.
Neijssen et al. (Mar. 3, 2005) "Cross-Presentation by Intercellular Peptide Transfer Through Gap Junctions," *Nature* 434:83-88.
Nguyen et al. (Dec. 10, 2004) "Inhibition of Gap Junction Activity Through the Release of the C1B Domain of PKCγ from 14-3-3: Identification of PKCγ Binding Sites," *J. Biol. Chem.* 279(50):52714-52725.
O'Byrne et al. (1998) "Phase II Study of Liarozole in Advanced Non-Small Cell Lung Cancer," *Eur. J. Cancer* 34(9):1436-1466.
Osborne et al. (2004) "Retinal Ischemia: Mechanisms of Damage and Potential Therapeutic Strategies," *Prog. Retin. Eye Res.* 23:91-147.
Queener et al. (Oct. 1993) "8-Aminoquinolines Effective Against *Pneumocyctis carinii* In Vitro and In Vivo," *Antimicrobial Agents Chemother.* 37(10):2166-2172.
Rapp et al. (Web Release Feb. 22, 2006) "Antitrypanosomal Activity of 5'-Deoxy-5'-(iodomethylene)adenosine and Related 6-N-Cyclopropyladenosine Analogues," *J. Med. Chem.* 49:2096-2102.
Rossi et al. (Nov. 2007) "Astrocyte Metabolism and Signaling During Brain Ischemia," *Nat. Neurosci.* 10(11):1377-1386.
Ruch, R.J. (1994) "The Role of Gap Junctional Intracellular Communication in Neoplasia," *Ann. Clin. Lab. Sci.* 24(3):216-231.
Ruch et al. (1993) "Reversal of *Ras*-Induced Inhibition of Gap-Junctional Intracellular Communication, transformation, and Tumorigenesis by Lovastatin," *Mol. Carcinog.* 7(1):50-59.
Saez et al. (2003) "Increased Gap Junctional Intercellular Communication is Directly Related to the Anti-Tumor Effect of all-Trans-Retinoic Acid Plus Tamoxifen in a Human Mammary Cancer Cell Line," *J. Cell. Biochem.* 89(3):450-461.
Seigel et al. (Apr. 2040) "Neuronal Gene Expression and Function in the Growth-Stimulated R28 Retinal Precursor Cell Line," *Curr. Eye Res.* 28(4):257-269.
Shi et al. (Web Release Apr. 13, 2008) "Synthesis and Anti-Breast Cancer Activities of Substituted Quinolines," *Bioorg. Med. Chem. Lett.* 18:3364-3368.
Singh et al. (2001) "Cell-Specific Caspase Expression by Different Neuronal Phenotypes in Transient Retinal Ischemia," *J. Neurochem.* 77:466-475.
Sosinsky et al. (Web Release Apr. 19, 2005) "Structural Organization of Gap Junction Channels," *Biocheim. Biophys. Acta* 1711:99-125.
Srinivas et al. (Mar. 2005) "Correlative Studies of Gating in Cx46 and Cx50 Hemichannels and Gap Junction Channels," *Biophys. J.* 88(3):1725-1739.
Steck, E.A. (1972) "Primaquine: Antimalarial Activity," In; *The Chemotherapy of Protozoan Diseases*, vol. III U.S. Army Medical Research and Development Command, Washington, D.C., p. 23.141-23.145.
Thompson et al. (May 12, 2006) "Ischemia Opens Neuronal Gap Junction Hemichannels," *Science* 312:924-927.
Trager et al. (Aug. 1980) "*Plasmodium falciparum*: Antimalarial Activity in Culture of Sinefungin and Other Methylation Inhibitors," *Exp. Parasitol.* 50(1):83-89.
Trosko et al. (2001) "Mechanism of Up-Regulated Gap Junctional Intracellular Communication During Chemoprevention and Chemotherapy of Cancer," *Mutat. Res.* 480-481:219-229.
Trosko et al. (1990) "Chemical, Oncogene and Growth Factor Inhibition Gap Junctional Intercellular Communication: An Integrative Hypothesis of Carcinogenesis," *Pathobiology* 58(5):265-278.
Unger et al. (Feb. 19, 1999) "Three-Dimensional Structure of a Recombinant Gap Junction Membrane Channel," *Science* 283:1176-1180.
van Riemsdijk et al. (2002) "Atovaquone Plus Chloroguanide Versus Mefloquine for Malaria Prophylaxis: A Focus on Neuropsychiatric Adverse Events," *Clin. Pharmacol. Therapeutics* 72(3):294-301.
Velaquez et al. (2003) "Gap Junctions and Neuronal Injury: Protectants or Executioners," *Neuroscientist* 9(1):5-9.
Veyssier et al. (2005) "Dihydrofolate Reductase Inhibitors, Nitroheterocycles (furans) and 8-Hydroxyquinolines," *Antimicrobial Agents* 35:941-963.
von Dieter Sicker et al. (1996) "59. Ein Alternativer Zugang Zum PQQ-Triester," *Helv. Chim. Acta.* 79:658-662.
Wang et al. (Jan. 20, 1995) "Purification and Characterization of Hypoxia-Inducible Factor 1," *J. Biol. Chem.* 270(3):1230-1237.
Wei et al. (Web Release Nov. 15, 2007) "Influences of Lovastatin on Membrane Ion Flow and Intracellular Signaling in Breast Cancer Cells," *Cell Mol. Biol. Lett.* 12(1):1-15.
White et al. (Aug. 13, 1998) "Connexin Mutations in Deafness," *Nature* 394:630-631.
Wiesner et al. (2003) "New Antimalarial Drugs," *Angew. Chem. Int. Ed.* (42):5274-5293.
Wilgenbus et al. (1992) "Expression of Cx26, Cx 32 and Cx43 Gap Junction Proteins in Normal and Neoplastic Human Tissues," *Int. J. Cancer* 51(4):522-529.
Yamasaki et al. (1996) "Role of Connexin Genes in Growth Control," *Carcinogenesis* 17(6):1199-1213.
Zhang et al. (Jan. 2002) "Angiogenesis Inhibitors Specific for Methionine Aminopeptidase 2 as Drugs for Malaria and Leishmaniasis," *J. Biomed. Sci.* 9(1):3440.
Zhu et al. (Nov. 1992) "Growth Retardation in Glioma Cells Concultured with Cells Overexpressing a Gap Junction Protein," *Proc. Nat. Acad. Sci. USA* 89(21):10218-10221.
Zucker et al. (2002) "Mutagenic Approaches to Modifying Gap Junction Phenotype," *Curr. Drug Targets* 3(6):441-453.
Paul et al. (1976) "5-Aryloxy-6-methoxy-8-aminoquinolines as Potential Prophylactic Antimalarials," *J. Pharmaceutical Sciences* vol. 65, No. 10:1527-1530.
Johnson et al. (1983) "Synthesis and Antileishmanial Activity of 6-Methoxy-4-methyl-N-[6-(substituted-1-piperazinyl)hexyl]-8-quinolinamines and Related Compounds,"*J. Med. Chem* 26:185-194.

* cited by examiner

**Effect of PQ analogs on *T. brucei* growth**

FIG. 1

A. MDA-MB-453 Cells

B. T47D Cells

*p< 0.05

Effect of PQ1 compound on the activation of Caspase 3 in T47D cells

*p< 0.05

COMPOUNDS AFFECTING GAP JUNCTION ACTIVITY

CROSS-REFERENCE TO RELATED APPLICATIONS

This application is a continuation-in-part of International Application number PCT/US2007/067652, filed Apr. 27, 2007, which claims priority to U.S. provisional application Ser. No. 60/745,909, filed Apr. 28, 2006 and U.S. provisional application Ser. No. 60/910,593 filed Apr. 6, 2007 which are all hereby incorporated by reference to the extent not inconsistent with the disclosure herewith.

REFERENCE TO FEDERAL FUNDING

This invention was sponsored, at least in part, by grant Nos. RO1 EY13421, P20RR017686, R01AG025500 and CA86842 from the National Institutes of Health. The US government has certain rights in this invention.

BACKGROUND OF THE INVENTION

Malaria and other parasitic diseases are serious public health problems. The known antimalarial agent, mefloquine, and its analogs have serious side effects including depression, psychotic episodes, and suicidal episodes. Because of these serious side effects, there have been attempts to formulate alternative antiparasitic compounds. Several approaches have attempted to use a quinoline structure and the primaquine branched 8-amino(1-alkyl)amino group. U.S. Pat. No. 4,980,360 discloses quinoline compounds having the primaquine 8-amino-1-methylbutylamino group which are reported for malaria treatment. U.S. Pat. Nos. 4,431,807 and 4,617,394 disclose quinoline compounds having a primaquine-like branched 8-aminoalkylamino group which are reported for treatment of malaria. U.S. Pat. No. 7,145,014 discloses quinoline compounds having an 8-[(4-amino-1-methylbutyl (amino) group. U.S. Pat. No. 6,376,511 discloses certain branched 8-aminoquinolines for the treatment of parasitic infections. U.S. Pat. No. 6,479,660 discloses methods of making certain antimalarial drugs. Other quinolines designed for the treatment of malaria are described in LaMontagne, J. Med. Chem. 1989, 32, 1728-1732.

Until recently, there was little information on the link between the structure of these antimalarial drugs and their detrimental psychological properties. It was discovered recently that mefloquine inhibits gap junctions, such as connexins 50 (Cx50). Gap junctions are the electrical synapses in neurons and responsible for neural transmission. They are non-specific membrane channels between cells and allow the passage of small molecules and ions from one cell to the next. Most tissues are coupled together by gap junctions that vary in type from cell to cell. Gap junctions are made up of hexamers of gap junction proteins, called connexins, abbreviated as Cx and named for their approximate size. Each hexamer hemichannel docks to another on an adjacent cell to form a complete channel or connexin. Connexin mutations have led to a number of human diseases, such as neurosensory autosomal recessive deafness, and the development of cardiovascular abnormalities.

The disruption of gap junctions produces serious neurological effects and is seen in neurodegenerative diseases such as Parkinson's disease and psychological diseases. Gap junction inhibitors are used to treat ischemic injury, such as stroke or during retinal surgery. Most, if not all, tumor cells have dysfunctional gap junctional intercellular communication (GJIC). Restoring GJIC is linked to drug sensitivity and reduction of tumorigenicity. The information regarding gap junction activity should be useful in development of new compounds that can be used to restore gap junction communication, or inhibit gap junction communication, depending on the disruption. New compounds that affect gap junctions are needed.

SUMMARY OF THE INVENTION

Provided are quinoline-based compounds. In one embodiment, provided are compounds having the following structure:

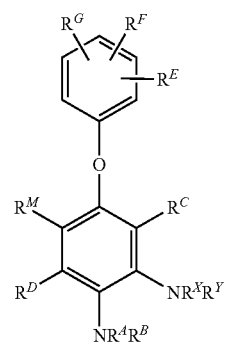

where $R^X$ and $R^Y$ are both oxygen or both hydrogen, or are independently selected from the group consisting of: hydrogen, —$(CH_2)_n$—$(X)_m$—Y, where n is an integer from 0-6; m is an integer from 0-2; X is independently —O—, —C(=O)—, —C(=NH)—, —S—, —S(=O)—, —SO$_2$—; and Y is selected from the group consisting of: hydrogen, optionally substituted C1-C6 straight chain or branched alkyl or alkoxy and nitrogen containing groups including —NH$_2$, —NO$_2$, —CN, phthalimide, imidazole, pyrazole, pyridine, pyrimidine, pyrazine, and pyridazine;

$R^C$, $R^D$ and $R^M$ are independently selected from the group consisting of: hydrogen, halogen, aldehyde, ketone, alcohol, optionally substituted C1-C6 straight chain or branched alkyl or alkoxy, RS—, RS(O)—, and RSO$_2$—, where the optional substituents are independently halogen, —S—, —S(O)—, or —SO$_2$—;

$R^E$, $R^F$, and $R^G$ are independently hydrogen, aldehyde, ketone, alcohol, optionally substituted C1-C6 straight chain or branched alkyl or alkoxy group, oxygen, halogen, CF$_3$, R$_2$N, RS—, RS(O)—, and RSO$_2$—, where the optional substituents are independently halogen, alcohol, CF$_3$, R$_2$N, —S—, —S(O)—, and —SO$_2$—, and where any $R^E$, $R^F$, or $R^G$ which is not hydrogen may be positioned in the ortho-, meta- or para-position;

$R^A$ and $R^B$ are both oxygen or both hydrogen, or are independently selected from the group consisting of: hydrogen, —$(CH_2)_n$—$(X)_m$—Y, where n is an integer from 0-6; m is an integer from 0-2; X is independently —O—, —C(=O)—, —C(=NH)—, —S—, —S(=O)—, —SO$_2$—; and Y is selected from the group consisting of: hydrogen and nitrogen containing groups including —NH$_2$, —NO$_2$, —CN, phthalimide, imidazole, pyrazole, pyridine, pyrimidine, pyrazine, and pyridazine;

or both $R^X$ and $R^Y$ and $R^C$ are optionally substituted carbon ring atoms which form a six membered ring where the optional substituents are hydroxyl, halogen, C1-C6 alkyl, ketone, ether, nitro, alkylsulfanyl, alkylsulfinyl, alkylsulfonyl, arylsulfanyl, arylsulfinyl, and arylsulfonyl, wherein when $R^X$, $R^Y$ and $R^C$ form a ring structure, $R^A$ and $R^B$ are not both oxygen or hydrogen.

In an embodiment, $R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen, C1-C6 straight chain or branched alkyl or alkoxy group and optionally substituted nitrogen containing groups including —NH$_2$, —NR$_2$, —NO$_2$, —CN, phthalimide, imidazole, pyrazole, pyridine, pyrimidine, pyrazine, and pyridazine, where the optional substituents include C1-C6 straight chain or branched alkyl or alkoxy group, oxygen, or halogen, where R is independently in each instance H, C1-C6 optionally substituted straight chain or branched alkyl or alkoxy group, or halogen.

In embodiments, the variables are as shown in the structures disclosed herein. In embodiments, the compounds of the invention are those compounds shown herein. Specific groups of alkyl are C1-C6, C7-C12 and all individual values and subgroups therein. "Aryl" takes its usual meaning known in the art and is generally a group containing an aromatic ring. When the substituent "R" is used herein without further specificity, it is understood that any group that may be structurally and synthetically possible, including those groups identified as $R^C$ or $R^E$ above, may be used, as known by one of ordinary skill in the art. Compounds previously described with an enabling disclosure are not intended to be claimed as compounds, but are intended to be included in methods of treatment described and claimed here to the fullest extent possible.

In one embodiment, provided are compounds having the following structure:

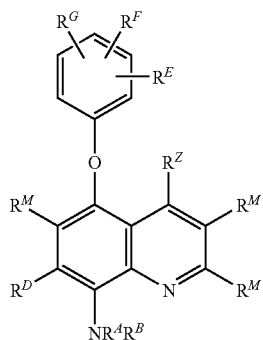

where $R^Z$, $R^M$ and $R^D$ are independently selected from the group consisting of: hydrogen, halogen, aldehyde, ketone, alcohol, optionally substituted C1-C6 straight chain or branched alkyl or alkoxy, nitro, amine, alkylsulfanyl, alkylsulfinyl, alkylsulfonyl, arylsulfanyl, arylsulfinyl, and arylsulfonyl, where the optional substituents are independently halogen nitro, amine, alkylsulfanyl, alkylsulfinyl, alkylsulfonyl, arylsulfanyl, arylsulfinyl, or arylsulfonyl;

$R^E$, $R^F$, and $R^G$ are independently hydrogen, aldehyde, ketone, alcohol, optionally substituted C1-C6 straight chain or branched alkyl or alkoxy group, oxygen, halogen, CF$_3$, R$_2$N, RS—, RS(O)—, and RSO$_2$—, where the optional substituents are independently halogen, alcohol, CF$_3$, R$_2$N, —S—, —S(O)—, and —SO$_2$— and where any $R^E$, $R^F$, or $R^G$ which is not hydrogen may be positioned in the ortho-, meta- or para-position;

$R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen, optionally substituted C1-C6 straight chain or branched alkyl or alkoxy, and nitrogen containing groups including —NH$_2$, —NO$_2$, —CN, phthalimide, imidazole, pyrazole, pyridine, pyrimidine, pyrazine, and pyridazine.

In an embodiment, $R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen, C1-C6 straight chain or branched alkyl or alkoxy group and optionally substituted nitrogen containing groups including —NH$_2$, —NR$_2$, —NO$_2$, —CN, phthalimide, imidazole, pyrazole, pyridine, pyrimidine, pyrazine, and pyridazine, where the optional substituents include C1-C6 straight chain or branched alkyl or alkoxy group, oxygen, or halogen, where R is independently in each instance H, C1-C6 optionally substituted straight chain or branched alkyl or alkoxy group, or halogen.

In one embodiment, provided are compounds having the formula:

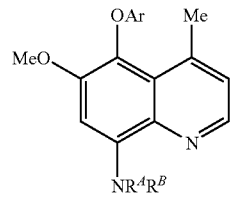

where Ar is o-, m- or p-C$_6$H$_4$CF$_3$;

$R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen, optionally substituted C1-C6 straight chain or branched alkyl or alkoxy, and nitrogen containing groups including —NH$^2$; —NR$_2$, where R is C1-C6 alkyl; —NO$_2$; —CN; phthalimide; imidazole; pyrazole; pyridine; pyrimidine; pyrazine; and pyridazine.

As used herein, an "alkoxy group" is a carbon chain where one or more carbon chain atoms is replaced with oxygen. An oxygen may be the first atom in the chain (i.e., the atom which bonds to the remainder of the molecule), or may be somewhere else in the chain.

In one embodiment, $R^A$ is hydrogen and $R^B$ is not hydrogen. In one embodiment, $R^Z$ is C1-C6 alkyl. In one embodiment, $R^Z$ is methyl. In one embodiment, $R^E$ and $R^G$ are hydrogen and RF is trifluoromethyl. In one embodiment, $R^E$ and $R^G$ are hydrogen and $R^F$ is m-trifluoromethyl. In one embodiment, $R^M$ is methoxy. In one embodiment, $R^M$ is C1-C3 alkoxy. In one embodiment, $R^A$ is hydrogen, and $R^B$ is a nitrogen-containing substituent.

A nitrogen-containing substituent is any substituent which contains nitrogen, including a nitro- or amino-containing group such as —NO$_2$; —NH$_2$; —CN; a ring-containing substituent such as imidazole, phthalimido, pyridine, pyrimidine, pyrazine, pyridazine- and NR$_2$, where one or more of the R's is not hydrogen such as a C1-C6 straight chain alkyl or alkoxy chain terminated by a nitrogen-containing substituent, such as those described here.

In the compounds of the invention, all possible combinations of variables are intended to be disclosed to the same extent as if they were each individually drawn.

Also provided is compound PQ1. Also provided is compound PQ2. Also provided is compound PQ3. Also provided is compound PQ4. Also provided is compound PQ5. Also provided is compound PQ6. Also provided is compound PQ7. Also provided is compound PQ8. Also provided is compound 13. Also provided is compound 14. Also provided is compound 15. Also provided is compound 17. Also provided is compound 18. Also provided is compound 21. Also provided is compound 22. Also provided is compound 23. Also provided is compound 24.

All substituents in the compounds of the invention may be optionally substituted with suitable substituents as known in the art. For example, in an alkyl chain, one or more of the carbons in the chain may be substituted with oxygen. Also, in an alkyl chain, one or more of the hydrogens may be substituted with a halogen, a C1-C6 optionally substituted straight chain or branched alkyl or alkoxy group, and so on. Also, any ring substituent may be positioned at the ortho-, meta- or para-position, as permitted by the other ring substituents, even if all locations are not specifically mentioned.

Also provided are methods for treating a gap junction disorder comprising administering an effective amount of a compound having a formula included herein to a patient. The patient may be a mammal, such as a mouse, rabbit, dog, cat, cow, pig, monkey, or human. The compound used to treat a gap junction disorder may be combined with a pharmaceutically acceptable carrier or other pharmaceutically acceptable additives, as known in the art.

In an embodiment, provided is a method for reducing retinal cell apoptosis, comprising administering an effective amount of a compound disclosed herein to a patient. In one embodiment, the compound has formula:

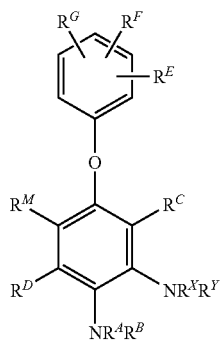

where $R^X$ and $R^Y$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen and nitrogen containing groups including —NH$_2$, —NO$_2$, —CN, phthalimide, imidazole, pyrazole, pyridine, pyrimidine, pyrazine, and pyridazine;

$R^C$, $R^D$ and $R^M$ are independently selected from the group consisting of: hydrogen, halogen, aldehyde, ketone, alcohol, optionally substituted C1-C6 straight chain or branched alkyl or alkoxy, nitro, amine, alkylsulfanyl, alkylsulfinyl, alkylsulfonyl, arylsulfanyl, arylsulfinyl, and arylsulfonyl, where the optional substituents are independently halogen, nitro, amine, alkylsulfanyl, alkylsulfinyl, alkylsulfonyl, arylsulfanyl, arylsulfinyl, and arylsulfonyl;

$R^E$, $R^F$, and $R^G$ are independently hydrogen, aldehyde, ketone, alcohol, optionally substituted C1-C6 straight chain or branched alkyl or alkoxy group, oxygen, halogen, nitro, amine, alkylsulfanyl, alkylsulfinyl, alkylsulfonyl, arylsulfanyl, arylsulfinyl, and arylsulfonyl, where the optional substituents are independently halogen, alcohol, nitro, amine, alkylsulfanyl, alkylsulfinyl, alkylsulfonyl, arylsulfanyl, arylsulfinyl, and arylsulfonyl, and where any $R^E$, $R^F$, or $R^G$ which is not hydrogen may be positioned in the ortho-, meta- or para-position; $R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen and nitrogen containing groups including —NH$_2$, —NO$_2$, —CN, phthalimide, imidazole, pyrazole, pyridine, pyrimidine, pyrazine, and pyridazine; or both $R^X$ and $R^Y$ and $R^C$ are optionally substituted carbon ring atoms which form a six membered ring where the optional substituents are hydroxyl, halogen, and C1-C6 alkyl, wherein when $R^X$, $R^Y$ and $R^C$ form a ring structure, $R^A$ and $R^B$ are not both oxygen or hydrogen.

In an embodiment, $R^A$ and $R^B$ are both oxygen or both hydrogen, or are independently selected from the group consisting of: hydrogen, —(CH$_2$)$_n$—(X)$_m$—Y, where n is an integer from 0-6; m is an integer from 0-2; X is independently —O—. —C(=O)—, —C(=NH)—, —S—, —S(=O)—, —SO$_2$—; and Y is selected from the group consisting of: hydrogen, C1-C6 straight chain or branched alkyl or alkoxy group and optionally substituted nitrogen containing groups including —NH$_2$, —NR$_2$, —NO$_2$, —CN, phthalimide, imidazole, pyrazole, pyridine, pyrimidine, pyrazine, and pyridazine, where the optional substituents include C1-C6 straight chain or branched alkyl or alkoxy group, oxygen, or halogen, where R is independently in each instance H, C1-C6 optionally substituted straight chain or branched alkyl or alkoxy group, or halogen.

In an embodiment, the method of reducing retinal cell apoptosis comprises administering a compound disclosed herein to a patient in an effective amount. In an embodiment, the method of reducing retinal cell apoptosis comprises administering a compound of formula PQ1 to a patient in an effective amount. "Reducing retinal cell apoptosis" means a reduction in the amount of retinal cells which undergo apoptosis. In an embodiment, administration of a compound of described herein reduces the number of retinal cells which undergo apoptosis under a certain condition as compared to cells which are not treated. "Reducing retinal cell apoptosis" does not mean no cells undergo apoptosis. Although applicant does not wish to be bound by theory, reduction in retinal cell apoptosis is believed to occur through inhibition of gap junction activity using the compounds described herein.

As used herein, a "gap junction disorder" is a disorder or effect of a treatment of a disorder which results in the abnormal activity of gap junctions. Examples of gap junction disorders that are caused by Cx50 are cataracts, retinitis pimentosa, SCA14, a type of neurodegenerative disorder known also as apinocerebellar ataxia. There is also a genetic link for Cx50 to certain forms of schizophrenia. The most common form of deafness is caused by mutations in the gap junction protein Cx26, but this protein is not acted upon by mefloquine drugs. Therefore, the current compounds and methods are especially important since they can treat gap junction disorders which are not treated by currently known drugs. Other examples of gap junction disorders include cancer, where the decreased gap junction activity of cancerous cells allows abnormal cell proliferation and growth. Another example of a gap junction disorder is treatment of several parasitic diseases with current drugs which inhibit the gap junction activity and cause undesirable neurological effects. Gap junction disorders can be treated by administering an effective amount of a compound or composition of the invention which affects the gap junction activity. As used herein, "treating" a gap junction disorder only means the gap junction activity is altered so as to cause a reduced effect of the gap junction disorder, not necessarily that the gap junction disorder is completely resolved. Treating a gap junction disorder includes increasing the gap junction activity of cells, decreasing the inhibition of gap junction activity as compared to other compounds, and other effects which are easily understood by one of ordinary skill in the art using the disclosure herewith.

As used herein, "parasite" means any organism which may infect any other organism and cause a deleterious effect. Parasite includes the organisms which cause malaria, *Trypanosomal brucei*, bird flu, and dengue virus.

Compounds which are specifically claimed are not intended to include compounds known in the art. Methods for using compounds of the invention may include compounds known in the art which are not known to be useful in the methods of the invention.

Compounds of the invention which are useful in providing improvement in gap junction disorders can be determined by routine testing which can be readily performed by one of ordinary skill in the art using methods known in the art and the guidance provided here.

BRIEF DESCRIPTION OF THE FIGURES

FIG. 1 shows inhibition of *T. brucei* growth using PQ1, PQ2, PQ3 and PQ4.

DETAILED DESCRIPTION OF THE INVENTION

Figure 2:
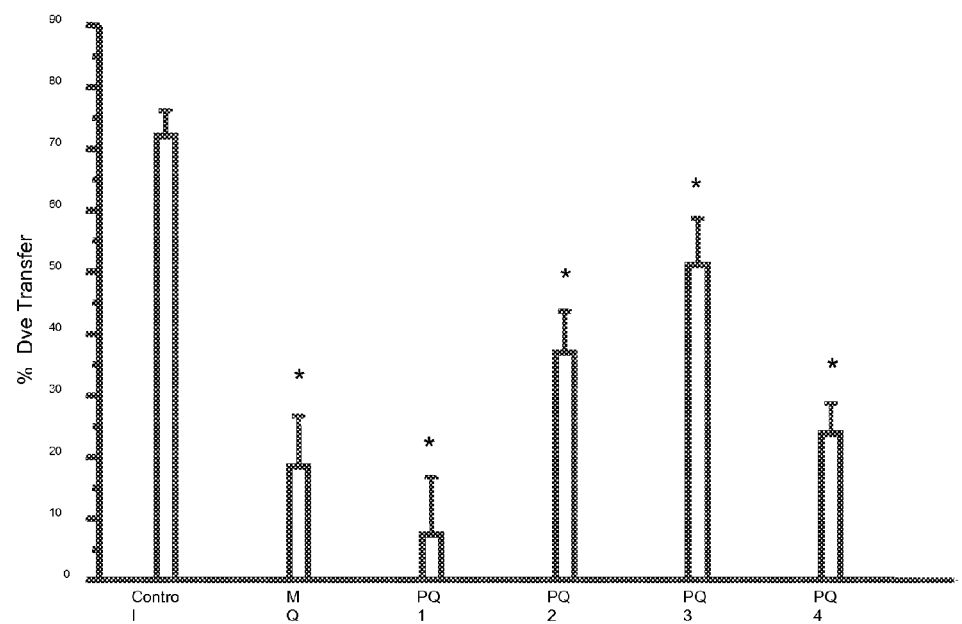
FIG. 2 shows the results of dye transfer/scrape loading experiments for R28 cells.

The following description provides nonlimiting examples of some embodiments of the invention.

Some specific compounds of the invention and discussed here are shown below.

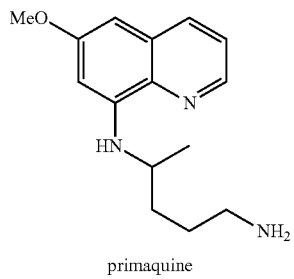

primaquine

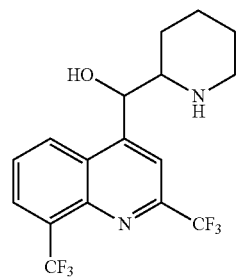

mefloquine

PQ1

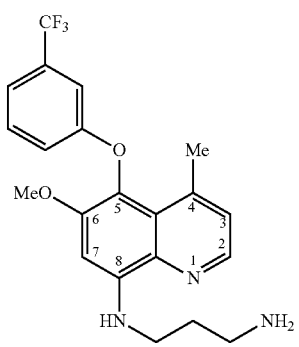

PQ2

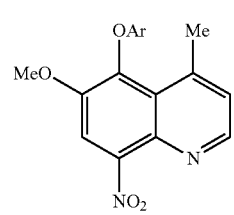

Ar = m-CF$_3$C$_6$H$_4$

PQ3

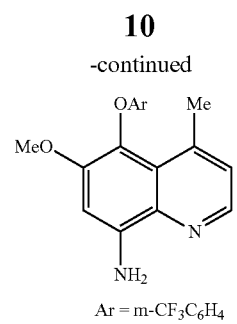

Ar = m-CF$_3$C$_6$H$_4$

PQ4

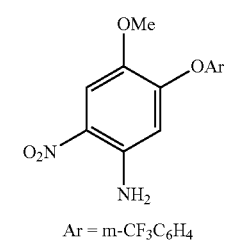

Ar = m-CF$_3$C$_6$H$_4$

PQ5

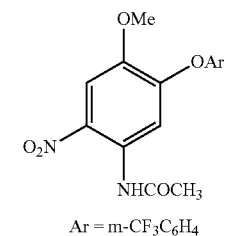

Ar = m-CF$_3$C$_6$H$_4$

PQ6

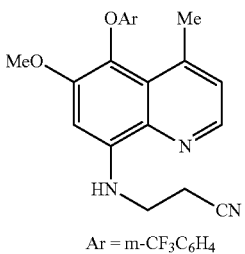

Ar = m-CF$_3$C$_6$H$_4$

PQ7

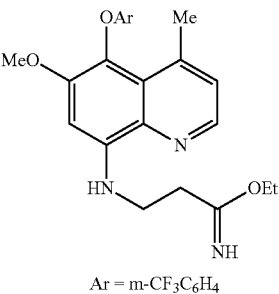

Ar = m-CF$_3$C$_6$H$_4$

PQ8

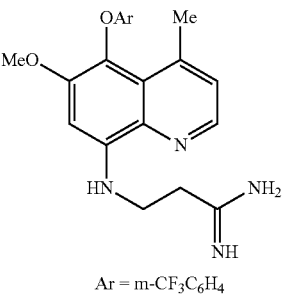

Ar = m-CF$_3$C$_6$H$_4$

-continued

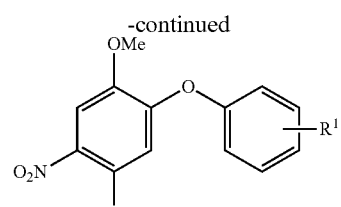

13: $R^1$ = OR; alkyl; $NR_2$
R is alkyl or phenyl

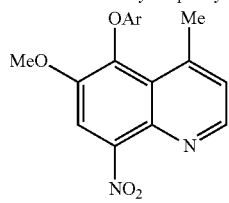

14: Ar = o-, m-, or p-$R^1C_6H_4$

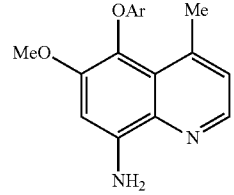

15: Ar = o-, m-, or p-$R^1C_6H_4$

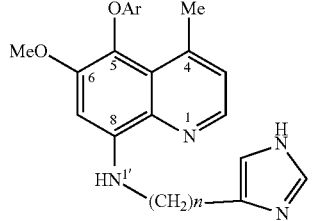

$HO_2C(CH_2)_2CO_2H$

17: Ar = o-, m-, or p-$R^1C_6H_4$
n = 1-2

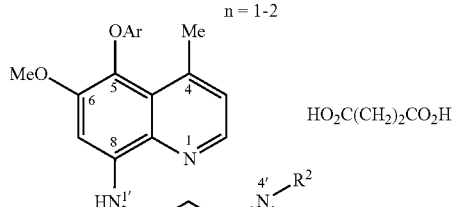

$HO_2C(CH_2)_2CO_2H$

18: Ar = m-$CF_3C_6H_4$; $R^3$ = H or Me;
$R^2$ = Me, Et, Pr;
$R^2, R^3$ = $(CH_2)_4$

All compounds disclosed herein include pharmaceutically acceptable salts, and pharmaceutically acceptable carriers.

One method for administering these compounds comprises the use of pharmaceutically acceptable salts, including those formed from the compounds of the invention and acids such as hydrochloric, hydrobromic, succinic, sulfamic, sulfuric, phosphoric, citric, tartaric, methanesulfonic, isethionic, aceturic, malic, fumaric, beta-resorcylic, or pamoic acid. Such salts may be administered orally in the form of tablets, capsules, or dragees when admixed with solid excipients such as lactose, sucrose, starch, microcrystalline cellulose, magnesium stearate or talc, nanogel which is any of a number of PEG-PEI (polyethylene glycol-polyethyleneimine) compounds. The foregoing compositions are preferred means for oral administration over the use of flavored syrups or tinctures containing the compound. Under certain circumstances, parenteral administration may be indicated, employing an aqueous solution or an oleaginous formulation of the agent. Aqueous solutions can be prepared in water, physiological saline, Ringer's solution, or the like, either with or without buffers. Oleaginous formulations may be made in natural oils (such as, peanut oil or olive oil), or in benzyl benzoate, for example.

EXPERIMENT ONE

Synthesis of Primaquine Analogs

Primaquine is a radical curative and causal prophylactic antimalarial agent, however, its toxicity has limited its usage as antimalarial agent. A class of primaquine analogs were synthesized and the synthetic scheme is depicted in Scheme 1. However, in the construction of PQ2 from PQ4, the ring closing reaction is not as straightforward as that reported. The synthetic procedure (vide infra) was modified and used to obtain a good yield of PQ2, which is needed for the synthesis of PQ3 and PQ1.

A reported synthesis (Lauer, W. M.; Rondestvedt, C.; Arnold, R. T.; Drake, N. L.; van Hook, J.; Tinker, J. Some derivatives of 8-aminoquinoline. J. Am. Chem. Soc. 1946, 48, 1546-1548) of a key intermediate, 2-bromo-4-acetamino-5-nitroanisole (6) was followed. Hence, 4-acetaminoanisole (5) was brominated with bromine in acetic acid (69% yield) followed by nitration with nitric acid in acetic anhydride and acetic acid (82% yield). Displacement of bromide 6 with potassium 3-trifluoromethylphenoxide (7) in N,N-dimethylformamide (DMF) at 120° C. gave 4-acetamino-5-nitro-2-(3-trifluoromethylphenyloxy)anisole (8). Removal of the acetyl protecting group of 8 with hydrochloric acid in ethanol afforded a 95% yield of 4-amino-5-nitro-2-(3-trifluoromethylphenyloxy)anisole (PQ4).

Scheme 1

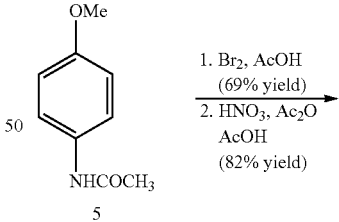

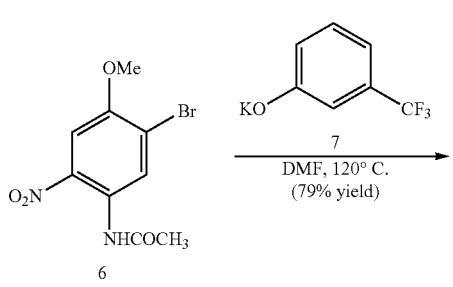

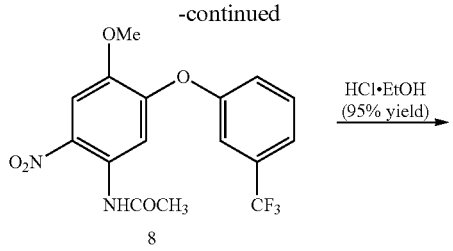

8

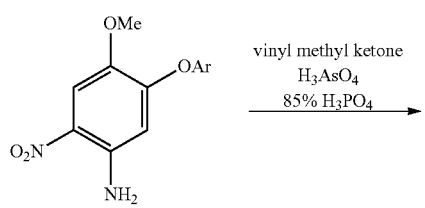

PQ4: Ar = m-CF$_3$C$_6$H$_4$

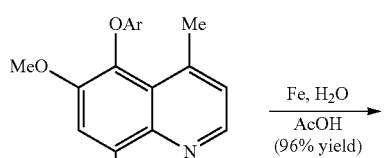

PQ2: Ar = m-CF$_3$C$_6$H$_4$

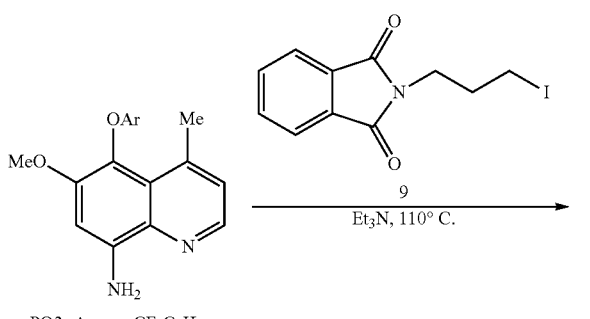

PQ3: Ar = m-CF$_3$C$_6$H$_4$

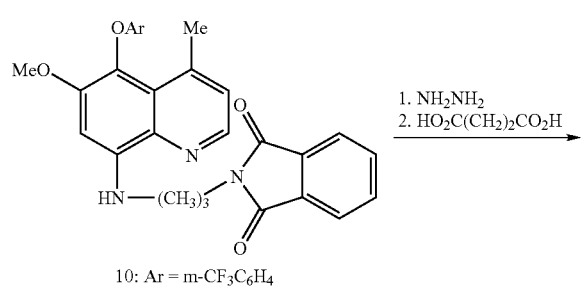

10: Ar = m-CF$_3$C$_6$H$_4$

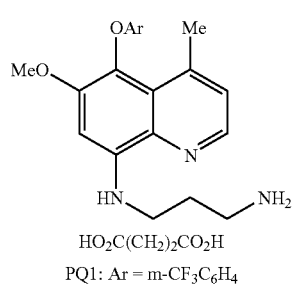

PQ1: Ar = m-CF$_3$C$_6$H$_4$

The ring closing reaction of PQ4 to PQ2 with vinyl methyl ketone is complex. When PQ4 was heated with vinyl methyl ketone, arsenic acid and phosphoric acid at 10° C. after 20 minutes, a mixture of PQ2, compound 11, and PQ4 in a ratio of 1:2:1 was obtained (Scheme 2). Longer reaction times resulted in decomposition of the products, and the use of excess of vinyl methyl ketone did not improve the yield. Compounds PQ2, 11, and PQ4 were separated by silica gel column chromatography. Treatment of compound 11 with arsenic acid and phosphoric acid at 10° C. for 20 minutes provided a mixture of PQ2, 11, and PQ4 in a ratio of 1:1:2. Likely, compound 11 underwent two reactions, cyclization to give compound 11 and reversed Michael reaction to give compound PQ4.

Scheme 2

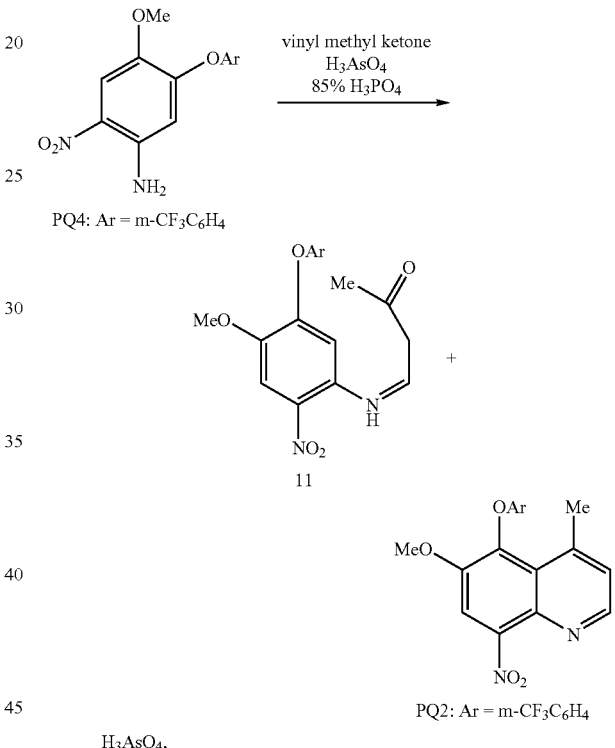

The synthesis of primaquine analogs was accomplished and previously unreported compounds including PQ1, were prepared. Hence, reduction of PQ2 with Fe in water and acetic acid afforded PQ3, which was alkylated with N-(3-iodopropyl)-phthalimide (9) to give compound 10. Removal of the phthalimide function of compound 10 with hydrazine followed by treatment with succinic acid furnished PQ1, which is soluble in water.

Other PQ1 Analogs

A number of further analogs of PQ1 were synthesized and some of these are depicted in Scheme 3. Michael addition of PQ3 with acrylonitrile in phenol (used as solvent) at 100° C. for 48 h afforded PQ6, which was converted into amidate PQ7 upon treatment with HCl in ethanol and benzene. PQ7 is transformed into imidate PQ8 with ammonia in THF in a sealed tube.

Scheme 3

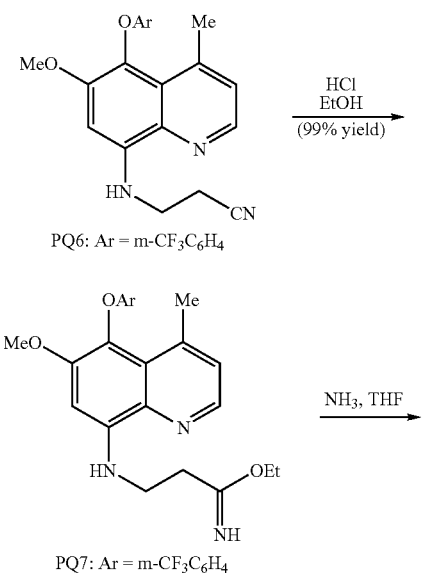

PQ3: Ar = m-CF$_3$C$_6$H$_4$

PQ6: Ar = m-CF$_3$C$_6$H$_4$

PQ7: Ar = m-CF$_3$C$_6$H$_4$

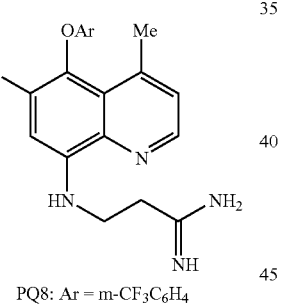

PQ8: Ar = m-CF$_3$C$_6$H$_4$

Similarly, other PQ analogs such as compounds 17 and 18 are synthesized (Scheme 4). Modification of the CF$_3$ and 4'-NH$_3$$^+$ moieties of PQ1 can readily be carried out using methods known to one of ordinary skill in the art. Compound 6 can be treated with various substituted phenoxides 12 containing electron donating (R$^1$=ortho-, meta-, or para-OR, alkyl, and NR$_2$) and withdrawing (R$^1$=CO$_2$R) groups, to give a series of compounds 13. Removal of the acetamide protecting group with HCl in ethanol followed by ring closing with vinyl methyl ketone and reduction of the nitro function furnish quinolines 15. Alkylation of the C8-amino function of compound 15 with 4-(chloromethyl)imidazole or 4-(chloroethyl)imidazole gives PQ analogs 17. Five different OAr groups used in the preparations of compounds 15 provide ten analogs 17, ie., a small library of PQ analogs is obtained. Beside imidazole analogs 16, 4-(chloromethyl)pyrazole, and 3-(chloromethyl)pyrazole can also be used. Heterocycles such as imidazole and pyrazole decrease the basicity of N4' of PQ1. N(4')-monosubstituted PQ1 analogs, compounds 18, are prepared from the alkylations of PQ1 (absence of succinic acid) with various alkyl bromides and triethylamine followed by salt-formation with succinic acid. The alkylamine nitrogen (4') of PQ1 is more basic (pK$_b$~3.2) than that of arylamine nitrogen(1') (pK$_b$~4.6), hence, alkylations take place on 4'-nitrogen. These modifications and others are readily carried out by one of ordinary skill in the art without undue experimentation using the methods described herein.

Scheme 4

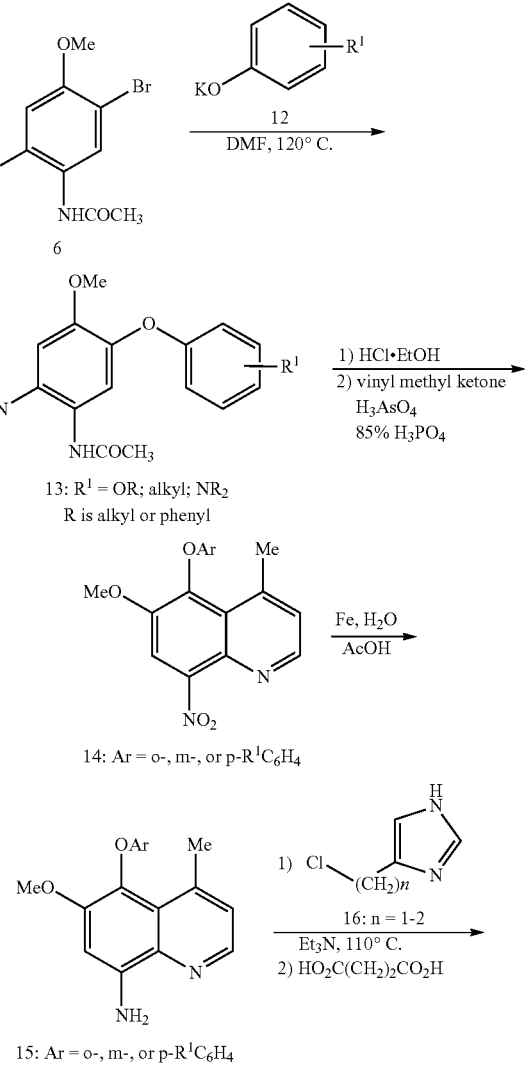

13: R$^1$ = OR; alkyl; NR$_2$
R is alkyl or phenyl

14: Ar = o-, m-, or p-R$^1$C$_6$H$_4$

15: Ar = o-, m-, or p-R$^1$C$_6$H$_4$

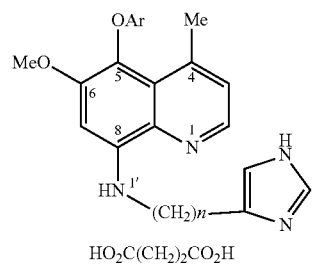

17: Ar = o-, m-, or p-R$^1$C$_6$H$_4$
n = 1-2

-continued

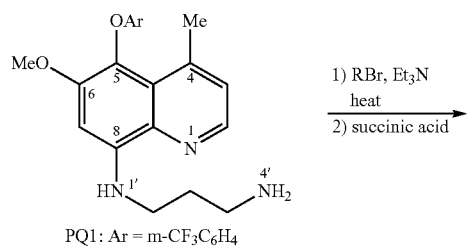

PQ1: Ar = m-CF$_3$C$_6$H$_4$

1) RBr, Et$_3$N heat
2) succinic acid

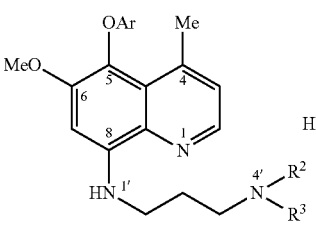

HO$_2$C(CH$_2$)$_2$CO$_2$H

18: Ar = m-CF$_3$C$_6$H$_4$; R$^3$ = H or Me;
R$^2$ = Me, Et, Pr;
R$^2$, R$^3$ = (CH$_2$)$_4$

The synthetic route shown here can lead to various analogs at C5 of PQ1, as known in the art. Two exemplary new classes of quinoline compounds were synthesized, quinolines 23 and 24, in which the m-trifluoromethylphenyloxy group was replaced with trifluoromethylphenyl and hydrogen, respectively (Scheme 5). Hence, the amide function of 6 was removed by the treatment of 12 N HCl in ethanol under reflux for 3 h to give a 99% yield of aniline 19. Cyclization of 19 with vinyl methyl ketone, arsenic acid, and phosphoric acid at 100° C. for 20 min gave a mixture of desired quinoline product 20 (38% yield) along with the debrominated product 21 (24% yield). Vinyl methyl ketone was added in portion to the reaction mixture to improve the yield of 20. Suzuki coupling reaction of bromide 20 with 3-trifluoromethylphenylboronic acid and 5% (tetrakis-triphenylphosphine)palladium and potassium carbonate in dioxane and water (degas) under argon afforded displacement product 22. Reduction of the nitro function of quinoline 22 with iron in acetic acid under reflux gave quinoline amine 23, which can be converted to various PQ1 analogs by either the S$_N$2 reaction with alkyl halides (or aryl halides) or reductive amination reaction with aldehydes. The debrominated quinoline 21 similarly was reduced to aminoquinoline 24, which again can be converted to various PQ1 analogs as that of 23 without C5-aryloxy moiety. It is well known in the art that other groups may be chosen and compounds may be prepared with various functionalities. For example, the amino group on compounds 23 and 24 can be replaced with —NR$^A$R$^B$ as described herein.

Scheme 5

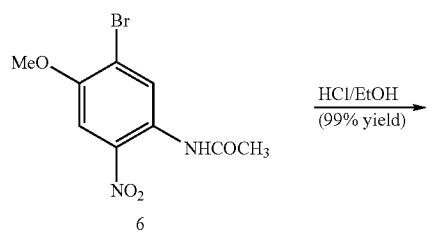

HCl/EtOH
(99% yield)

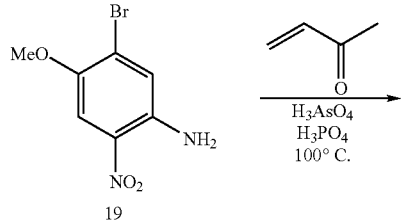

H$_3$AsO$_4$
H$_3$PO$_4$
100° C.

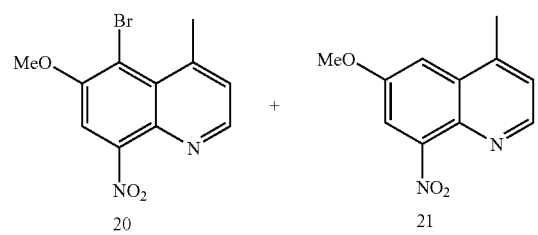

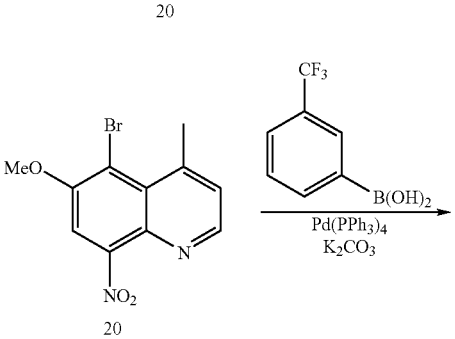

Pd(PPh$_3$)$_4$
K$_2$CO$_3$

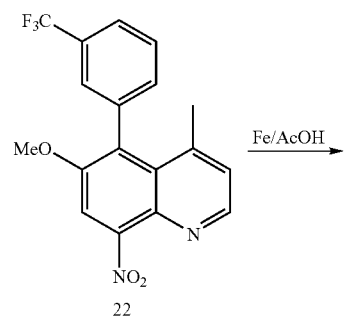

Fe/AcOH

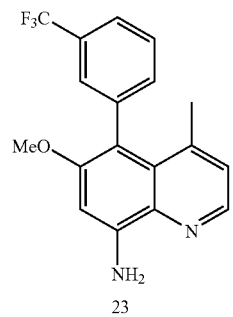

23

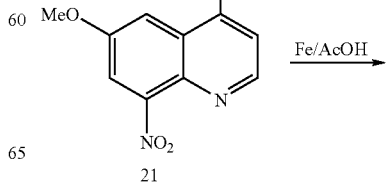

Fe/AcOH

-continued

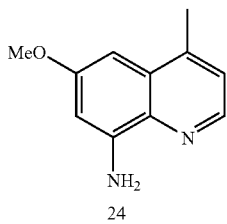

Synthetic Procedures

General procedure: 4-Acetaminoanisole, vinyl methyl ketone, 3-(trifluoromethyl)phenol, and arsenic acid were obtained from Aldrich Chemical Co. Potassium t-butoxide was prepared by treating t-butanol with potassium metal at 85° C. followed by evaporating excess of t-butanol under vacuum.

2-Bromo-4-acetaminoanisole. To a solution of 10.0 g (60.5 mmol) of 4-acetaminoanisole (5) in 80 mL of acetic acid, was added dropwise 11.6 g (72.7 mmol) of bromine and maintaining internal temperature of the reaction below 50° C. After stirring for 1 h, the reaction mixture was poured into 400 mL of ice-water containing 1.2 g of NaHSO$_3$. The mixture was stirred until yellow-red color disappeared and left at room temperature for overnight. The solid (product) was filtered, dried under vacuum at 70° C., and crystallized from ethanol to give 10.19 g (69% yield). $^1$H NMR (CDCl$_3$) δ 7.67 (d, J=2.5 Hz, 1 H), 7.44 (dd, J=9, 2.5 Hz, 1 H), 7.1 (bs, 1 H, NH), 6.85 (d, J=9 Hz, 1 H), 3.87 (s, 3 H, OMe), 2.16 (s, 3 H, CH$_3$).

2-Bromo-4-acetamino-5-nitroanisole (6). To a cold (5° C.) solution of 3.36 g (13.8 mmol) of 2-Bromo-4-acetaminoanisole in 5 mL of acetic anhydride and 10 mL of acetic acid, was added dropwise 0.9 mL (13.8 mmol) of concentrate nitric acid. The resulting solution was stirred at 5° C. for 3 h, poured into 90 mL of water, stirred, and filtered to collect the solid (the desired product). The solid was washed twice with cold water, dried under vacuo at 100° C., crystallized from chloroform to give 3.26 g (82% yield) of pure compound 6. $^1$H NMR (CDCl$_3$) δ 10.2 (s, 1 H, NH), 9.09 (s, 1 H), 7.67 (s, 1 H), 3.95 (s, 3 H, OMe), 2.28 (s, 3 H, CH$_3$).

Potassium 3-(trifluoromethyl)phenoxide (7). A mixture of 1.94 g (12 mmol) of 3-(trifluoromethyl)phenol and 1.344 g (12 mmol) of potassium t-butoxide was stirred under argon for 30 min. A solution was resulted, and the by-product, t-butanol, was removed under vacuum and heat to give a white solid.

4-Acetamino-5-nitro-2-(3-trifluoromethylphenyloxy)anisole (8). To the above solid 7 under argon, was added a solution of 3.0 g (10.4 mmol) of bromide 6 in 20 mL of DMF via cannula. The resulting solution was stirred at 120° C. for 1 day. TLC and NMR indicated the presence of a small amount of starting material 6. The reaction solution was cooled to room temperature and 2 mmol of compound 7 was added. The solution was stirred at 120° C. for 12 hour, diluted with 200 mL of ice and water, and the solid was collected by filtration, washed with water, dried under vacuum, and crystallized from ethanol to give 3.04 g (79% yield) of compound 8. $^1$H NMR (CDCl$_3$) δ 10.4 (s, 1 H, NH), 8.39 (s, 1 H), 7.83 (s, 1 H), 7.5 (m, 2 H), 7.3 (m, 2 H), 3.93 (s, 3 H, OMe), 2.23 (s, 3 H, CH$_3$). $^{13}$C NMR (CDCl$_3$) δ 174, 155.7, 153.9, 142.4, 141.6, 130.9, 123.0, 121.7, 121.6, (116.9, 116.8, 116.7, 116.6 q for CF$_3$), 108.7, 106.6, 56.7, 21.8.

4-Amino-5-nitro-2-(3-trifluoromethylphenyloxy)anisole (PQ4). A solution of 2.0 g (5.3 mmol) of compound 8 in 4 mL of concentrate HCl and 30 mL of ethanol was heated under argon at reflux for 2 hours. The solution was cooled to room temperature, poured into 200 mL of ice and water, and the orange solid was collected by filtration. The solid was washed with water twice and crystallized from ethanol to give 1.69 g (95% yield) of PQ4. $^1$H NMR (CDCl$_3$) δ 7.70 (s, 1 H), 7.5 (m, 2 H), 7.32 (m, 1 H), 7.20 (m, 2 H), 6.15 (s, 1 H), 3.87 (s, 3 H, OMe).

6-Methoxy-4-methyl-8-nitro-5-(3-trifluoromethylphenyloxy)quinoline (PQ2) and 4-{N-[4-methoxy-2-nitro-5-(trifluoromethylphenyloxy)]amino}2-butanone (11). To a flask equipped with a condenser and a thermometer, 2.0 g (6.0 mmol) of compound PQ4, 1.7 g (12 mmol) of H$_3$AsO$_4$, and 15 mL of 85% H$_3$PO$_4$ were added. The mixture was stirred and heated to 100° C. (bath temperature is 110° C.), and 0.7 mL of vinyl methyl ketone was added dropwise via syringe. The orange color of the solution turned to red color immediately. After stirring at 100° C. for 20 min, the reaction solution was cooled to room temperature, poured into ice and water, and the solid (HCl salt of the product) was collected by filtration. The solid was added to an aqueous NH$_4$OH—NaOH solution, stirred for 10 min, and the red solid was collected by filtration. The solid was washed with water twice and dried under vacuum to give a crude product. The above filtrates were combined, neutralized with NH$_4$OH—NaOH, and extracted with chloroform three times. The combined extract was washed with brine, dried (MgSO$_4$), concentrated, and combined with the above crude product. The combined crude product was separated by silica gel column chromatography using a mixture of hexane, diethyl ether, and dichloromethane as solvents to give 0.576 g (25% yield) of PQ2, 1.214 g (50% yield) of compound 11, and 0.50 g (25% recovery) of PQ4. Compound PQ2: $^1$H NMR (CDCl$_3$) δ 8.78 (d, J=4 Hz, 1 H), 7.88 (s, 1 H), 7.40 (m, 2 H), 7.27 (m, 1 H), 7.11 (s, 1 H), 6.93 (d, J=7 Hz, 1 H), 3.87 (s, 3 H, OMe), 2.74 (s, 3 H, Me). $^{13}$C NMR (CDCl$_3$) δ 158.0, 151.0, 148.3, 146.9, 143.8, 139.9, 136.3, 132.9, 132.3, 130.6, 126.0, 125.2, 121.1, (119.7, 119.6, 119.5, 119.4 for CF$_3$), 118.3, 112.5, 111.8, 57.3, 23.4.

Compound 11: $^1$H NMR (CDCl$_3$) δ 8.18 (s, 1 H), 7.78 (s, 1 H), 7.50 (m, 2 H), 7.30 (m, 2 H), 6.32 (s, 1 H), 3.87 (s, 3 H, OMe), 3.40 (t, J=7 Hz, 2 H), 2.75 (t, J=7 Hz, 2 H), 2.17 (s, 3 H, Me). $^{13}$C NMR (CDCl$_3$) δ 205.0, 151.0, 142.5, 141.6, 130.9, 122.2, 121.3, 121.2, 116.0, 111.8, 109.8, 103.0, 56.7, 42.6, 37.7, 30.5.

8-Amino-6-methoxy-4-methyl-5-(3-trifluoromethylphenyloxy)quinoline (PQ3).

To a solution of 0.20 g (0.53 mmol) of PQ2 in 0.1 mL of acetic acid and 10 mL of water, was added 0.18 g (3.2 mmol) of iron. The mixture was stirred and heated at 100° C. for 2 h, cooled to room temperature, extracted with dichloromethane three times. The combined extract was washed with aqueous NaHCO$_3$, brine, dried (MgSO$_4$), concentrated, and column chromatographed on silica gel using a mixture of hexane, dichloromethane, and diethyl ether as eluent to give 0.18 g (96% yield) of PQ3. $^1$H NMR (CDCl$_3$) δ 8.46 (d, J=4 Hz, 1 H), 7.34 (t, J=8 Hz, 1 H), 7.22 (d, J=8 Hz, 1 H), 7.15 (m, 2 H), 6.93 (d, J=8 Hz, 1 H), 6.79 (s, 1 H), 5.15 (bs, 2 H, NH$_2$), 3.80 (s, 3 H, OMe), 2.63 (s, 3 H, Me). $^{13}$C NMR (CDCl$_3$) δ 150.5, 145.6, 143.7, 142.8, 130.2, 125.1, 124.6, 118.3, 118.26, 118.2, (112.3, 112.2, 112.1, 112.0) (q, CF$_3$), 97.9, 56.6, 23.3.

6-Methoxy-8-(3-phthalimidopropylamino)-4-methyl-5-(3-trifluoromethylphenyloxy) quinoline (10). A solution of 2.0 g (5.7 mmol) of PQ3, 1.81 g (5.7 mmol) of 3-iodopropylphthalimide (9), and 0.58 g (5.7 mmol) of triethylamine in 15 mL of 2-ethoxyethanol was stirred under argon at 110° C. for 12 hours. The reaction mixture was cooled to room temperature, diluted with chloroform, and washed water and brine.

The organic layer was dried ($K_2CO_3$), concentrated to give compound 10 along with 1,3-diphthalimidopropane. The mixture was used in the next step without purification. Pure compound 10 can be obtained by dissolving the crude product in ether and HCl, and orange-red HCl salt was precipitated out. It was filtered and the solid was crystallized from ethanol to give pure 10.

6-Methoxy-8-[(3-aminopropyl)amino]-4-methyl-5-(3-trifluoromethylphenyloxy) quinoline succinic acid (PQ1). A solution of the above phthalimide 10 in 100 mL of 65% hydrazine and 100 mL of ethanol was refluxed under argon for 3 hours. After cooling to room temperature, the solution was diluted with 10% aqueous KOH solution and extracted with dichloromethane three times. The combined extract was washed with brine, dried ($K_2CO_3$), concentrated, and column chromatographed on silica gel using dichloromethane and methanol as eluants to give 1.86 g (80% yield) of 6-methoxy-8-[(3-aminopropyl)amino]-4-methyl-5-(3-trifluoromethylphenyloxy)quinoline. $^1H$ NMR ($CDCl_3$) δ 8.40 (d, J=4 Hz, 1 H), 7.34 (t, J=8 Hz, 1 H), 7.21 (d, J=8 Hz, 1 H), 7.06 (m, 2 H), 6.93 (d, J=8 Hz, 1 H), 6.48 (s, 1 H), 6.4 (bs, 1 H, NH), 3.83 (s, 3 H, OMe), 3.42 (t, J=8 Hz, 2 H), 2.99 (t, J=8 Hz, 2 H), 2.62 (s, 3 H, Me), 1.98 (pentet, J=8 Hz, 2 H), 1.80 (bs, 2 H, $NH_2$). $^{13}C$ NMR ($CDCl_3$) δ 160.0, 151.1, 145.0, 143.5, 142.7, 130.2, 125.2, 118.4, 118.2, 112.2, 107.5, 92.9, 56.8, 41.6, 40.4, 33.1, 23.4. The succinic acid salt was prepared by treating 0.457 g (1.12 mmol) of the quinoline with 0.134 g (1.13 mmol) of succinic acid in 10 mL of methanol. The resulting solution was concentrated to dryness, crystallized from diethyl ether to give a quantitative yield of the succinic acid salt PQ1.

6-Methoxy-8-[(2-cyanoethyl)amino]-4-methyl-5-(3-trifluoromethyl phenyloxy) quinoline (PQ6). A solution of 0.25 g (0.72 mmol) of PQ3, 38 mg (0.72 mmol) of acrylonitrile, and 3 g of phenol (Klenke, B.; Stewart, M.; Barrett, M. P.; Brun, R.; Gilbert, I. H. Synthesis and biological evaluation of s-triazine substituted polyamines as potential new anti-trypanosomal drugs. J. Med. Chem. 2001, 44, 3440-3452.)$_{1-2}$ was heated under argon at 100° C. for 48 h. The solution was cooled to room temperature, diluted with methylene chloride, washed with 1 N NaOH solution, and brine. The methylene chloride layer was dried ($MgSO_4$), concentrated, and column chromatographed on silica gel to give 0.203 g (70% yield) of PQ6. $^1H$ NMR ($CDCl_3$) δ 8.43 (d, J=4.5 Hz, 1 H), 7.35 (t, J=9 Hz, 1 H), 7.23 (d, J=7 Hz, 1 H), 7.12 (d, J=4.5 Hz, 1 H), 7.07 (s, 1 H), 6.94 (d, J=8 Hz, 1 H), 6.72 (t, J=6 Hz, 1 H), 6.52 (s, 1 H), 3.84 (s, 3 H, OMe), 3.77 (q, J=7 Hz, 2 H, $CH_2N$), 2.81 (t, J=7 Hz, 2 H, $CH_2CN$), 2.63 (s, 3H, $CH_3$).

6-Methoxy-8-[(2-(ethoxycarboiminoyl)ethylamino]-4-methyl-5-(3-trifluoromethylphenyloxy)quinoline (PQ7). To a cold (0° C.) solution of 63 mg (0.16 mmol) of PQ6 in 2 mL of ethanol and 2 mL of benzene, HCl gas was bubbled in via a tubing. The reaction vessel was sealed and stirred at room temperature for 3 days, cooled to 0° C., and diluted with 25 mL of ether. The precipitated solid was collected by filtration and dried to give 70 mg (99% yield) of PQ7. $^1H$ NMR ($CDCl_3$) δ 8.5 (bs, 1 H), 7.40 (m, 2 H), 7.30 (d, J=7 Hz, 1 H), 7.06 (s, 1 H), 6.90 (d, J=8 Hz, 1 H), 6.83 (s, 1 H), 4.20 (q, J=7 Hz, 2 H, $OCH_2$), 3.90 (s, 3 H, OMe), 3.71 (bs, 2 H, $CH_2N$), 3.05 (bs, 2 H, $CH_2CN$), 2.88 (s, 3 H, $CH_3$), 1.30 (t, J=7 Hz, 3 H, $CH_3$).

6-Methoxy-8-[(2-(amidinoylethyl)amino]-4-methyl-5-(3-trifluoromethylphenyloxy)quinoline (PQ8). A solution of PQ7 and $NH_3$ (excess) in ethanol was heated at 50° C. in a sealed tube to give PQ8.

EXPERIMENT TWO

Antiparasitic Activities

Figure 1:
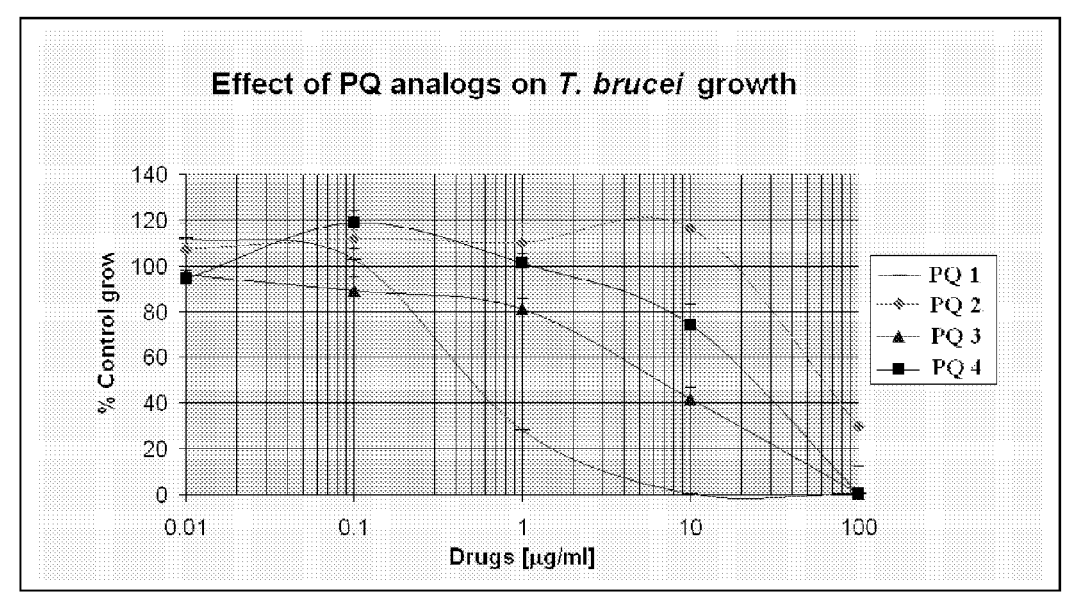

The antiparasitic activities of exemplary compounds described here was studied using the anti-trypanosomal activity protocol described in: Rapp M, et al. J Med Chem 2006; 49:2096-102. The $IC_{50}$ values of PQ1, PQ2, PQ3 and PQ4 against *Trypanosoma brucei* (*T. brucei*) are 340 ng/mL, 2,498 ng/mL, 1,083 ng/mL and 25 µg/mL. FIG. 1 summarizes the compound inhibition of *T. brucei* growth. It is seen that compounds of the invention are useful in inhibiting *T. brucei* growth.

Methods Used for Antiparasitic Activities

Plasmepsin assay: The substrate used for the plasmepsin assay (BACHEM) is a synthetic peptide (Dabcyl-Glu-Arg-Nle-Phe-Leu-Ser-Phe-Pro-Edans) designed to mimic the cleavage site present in hemoglobin. The kinetic constants for the substrate are $K_m$=0.78 $s^{-1}$ and $K_{cat}$=0.10 µM for *P. falciparum* plasmepsin, and $K_m$=0.69 s−1 and $K_{cat}$=0.16 µM for *P. vivax* plasmepsin. The substrate is conjugated with the fluorescent donor EDANS and the quencher DABCYL. Fluorescence is only detectable when the EDANS group is separated from the DABCYL group by cleavage of the substrate. (Unger, V. M.; Kumar, N. M.; Gilula, N. B.; Yeager, M. Three-dimensional structure of a recombinant gap junction membrane channel. Science, 1999, 283, 1176-1180; Fleishman, S. J.; Unger, V. M.; Ben-Tal, N. Transmembrane protein structures without X-rays. Trends in Biochem. Sci. 2006, 31, 106-113).

An automated plasmepsin assay protocol was developed that allowed screening of a large number of compounds within a short period of time. Compounds were manually added to 96-well plates followed by the addition of assay buffer (15 mM NaCl, 100 mM Formate, pH 4.4) using an automated dilutor (BioMec 2000 from BECKMAN). After thorough mixing and dilution, the contents of the plates were transferred to test plates and plasmepsin enzyme solution was added with the dilutor. After a ten-minute incubation at 37° C., background fluorescence was measured with a fluorescence plate reader (WALLAC Victor2). Finally, the substrate was added (final concentration of 10 µM) and the reaction mixture was incubated for 30 minutes at 37° C. followed by fluorescence detection. Each compound was tested in this prescreen in triplicate at the concentration of 10 µg/ml. Compounds that reduced the activity of plasmepsin by 50% or more at this concentration were selected for a second screen to determine $IC_{50}$ values. The best inhibitors were assayed using a range of inhibitor concentrations and substrate concentrations to determine $K_I$ values (ENZYME KINETICS from TRINITY SOFTWARE).

Culturing of Parasites. The bloodstream form of *Trypanosoma brucei* 427 strain was maintained under the standard cell culture conditions (37° C., 5% $CO_2$). The parasites were grown in complete HMI-9 medium containing 10% FBS, 10% Serum Plus and 1× Penicillin/Streptomycin. (Angew. Chem. Int. Ed. Engl. 2003, 42, 5274-5293).

Luciferase Assay. Luciferase assay was used to measure ATP-bioluminescence in *T. brucei* cultured in 96-well plates at 37° C. for 48 hours. Parasites were diluted to 1.0×10⁵ cells/mL in complete HMI-9 medium. One hundred microliters (100 µL) of the diluted parasites were aliquoted into sterile 96-well flat white opaque culture plates (Greiner). Each compound was serially diluted from 10 µM to 0.1 µM in DMSO and then mixed in the appropriate wells containing parasites. The treated parasites were then incubated for 48 hours at 37° C. with 5% $CO_2$ before monitoring viability. To measure the viability of the parasites after treatment with each compound, the parasites were lysed in the wells by adding 100 μL of CellTiter-Glo™ (Promega). After lysis, the ATP bioluminescence of the 96-well plates was measured with a SpectraFluor Plus multidetection plate reader (Tecan).

Malaria parasite *Plasmodium falciparum*: Culturing of *P. Falciparum* was carried out as described in: Trager, W., et al: Exp. Parasitol. 50: 83-89, 1980; and Zhang P et al. J Biomed Sci 2002; 9:34-40.

*P. falciparum* parasites were cultured by standard methods in RPMI medium supplemented with 10% serum or Albu-MAX I serum substitute (Gibco BRL) and a 2% hematocrit of human erythrocytes. Parasite synchrony was maintained by serial treatments with sorbitol. Two strains are used, 3D7 and W2; the former being susceptible to drugs, while the latter is resistant to chloroquine, sulfadoxine, pyrimethamine, and quinine. Other strains can be used, as well.

The isotopic method was followed with modifications. Two hundred microliters of the suspension of infected erythrocytes was distributed in triplicate in 96-well tissue culture plates that were either drug-free or pre-coated with test compounds. The parasites were incubated at 37° C. in 5% $CO_2$. [$^3$H]hypoxanthine (specific activity, 16.3 Ci/mmol; 1 μCi/well) was added after the first 18 h of incubation to assess parasite growth. The incorporation of [$^3$H]hypoxanthine has been established as an accurate and reliable means of determining in vitro parasite growth. After an additional 24 h of incubation, the plates were frozen to terminate the assays. The plates were thawed to lyse the infected erythrocytes, and the contents of each well were collected on glass-fiber filter papers, washed, and dried with a cell harvester. The filter disks were transferred into scintillation tubes, and 2 ml of scintillation cocktail was added. The incorporation of [$^3$H] hypoxanthine was quantitated with a liquid scintillation counter.

EXPERIMENT THREE

Studies of the Inhibitory Activities of Gap Junctions

Gap junctions provide a major cell-to-cell communication role in electrical synapses in neural systems (van Riemsdijk, M. M.; Sturkenboom, M. C. J. M.; Ditters, J. M.; Ligthelm, R. J.; Overbosch, D.; Stricker, B. H. Ch. *Clin. Pharmacol. & Therapeutics,* 2002, 72, 294-301). Gap junctions have been called both "Good Samaritans" and "Executioners" (Cruikshank, S. J.; Hopperstad, M.; Younger, M.; Connors, B. W.; Spray, D. C.; Srinivas, M. *PNAS* 2004, 101, 12364-12369), terms which refer to their ability to pass both necessary metabolites and apoptotic signals from one cell to another. The passage of apoptotic signals through open gap junctions has been linked to acute oxidative stress-induced neural cell death (Loewenstein, W. R. *Physiol. Rev.* 1981, 61, 829; White, T. W.; Deans, M. R.; Kelsell, D. P.; Paul, D. L. *Nature,* 1998, 394, 630). The "Bystander Effect" occurs when a dying adjacent cell delivers a cellular apoptotic signal such as low ATP or high $Ca^{+2}$ to an adjacent cell through uncontrolled open gap junctions. The process is well documented in cerebral ischemia, where the expansion of the ischemic infarct results from the transfer of ions and second messengers through astrocytes and other gap junction-containing neural cells. Inhibition of gap junctions can prevent neural cell death when used acutely (Britz-Cunningham, S. H.; Shah, M. M.; Zuppan, C. W.; Fletcher, W. H. *N. Engl. J. Med.* 1995, 332, 1323; Sosinsky, G. E.; Nicholson, B. J. Structural organization of gap junction channels. *Biochim. Biophys. Acta,* 2005, 1711, 99-125). It is apparent that proper control of gap junctions is required for neural health and that improper control would lead to neural toxicity. However, maintaining gap junctions in an open or closed state can both be neurotoxic. While closure of gap junctions would prevent the passage of apoptotic signals under acute stress, open gap junctions are required for the day-to-day control of neural cell signaling. Thus, long-term use of gap junction inhibitors would be neurotoxic.

A gap junction channel is composed of two anchored connexon hexamers of gap junction proteins (Cx's) which assemble into large and more functional cell surface aggregates of up to 10,000 hexamers connecting two adjacent cells and allowing passage of up molecules of up to 1000 daltons. Some Cx's, such as Cx50, also form hemichannels which communicate directly with the outside environment of the cell (Veenstra, R. D. *Recent Res. Devel. Biophys.* 2003, 2, 65-94; Beyer, E. C.; Paul, D. L.; Goodenough, D. A. Connexin family of gap junction proteins. *J. Membrane Biol.* 1990, 116, 187-194; Makowski, L.; Caspar, D. L. D.; Phillips, W. C.; Goodenough, D. A. *J. Cell Biol.* 1977, 74, 629-645; Bruzzone, R.; White, T. W.; Paul, D. L. *Eur. J. Biochem.* 1996, 238, 1; Unger, V. M.; Kumar, N. M.; Gilula, N. B.; Yeager, M. *Science,* 1999, 283, 1176-1180). Assembly and disassembly occurs in about 2 hr, and, can be stimulated by stress signals, pH, and phosphorylation by protein kinases such as PKCγ (Fleishman, S. J.; Unger, V. M.; Ben-Tal, N. *Trends in Biochem. Sci.* 2006, 31, 106-113).

In order to study gap junctions, several inhibitors have been used including 18-6-glyrrhetinic acid (AGA), which inhibits gap junction synthesis, and mefloquine, which preferentially blocks Cx50 gap junction activity. Mefloquine and related drugs have been used extensively by the military as antimalarial prophylactics. However, their side effects include depression, psychotic episodes, suicide, and general neurotoxicity.

To determine the effects of the compounds of the invention on gap junctions, human R28 cells and lucifer yellow dye and rhodamine dextran were used to study gap junction. (Das, S.; Lauer, J.; Barnett, M.; Lin, D.; Akoev, V.; Battina, S.; Hua, D. H.; Takemoto, D. J. PKCγ phosphorylates connexin50 on serine-430. A presentation at 2006 ARVO Annual Meeting, Apr. 30-May 4, 2006, Fort Lauderdale, Fla.). FIG. 2 shows R28 cells grown to 90% confluency on coverslips. The cells were treated with different compounds as shown @ 10 μM for 40 minutes. A mixture of lucifer yellow (LY) and rhodamine dextran (RD) was added to the cells at the center of the coverslip. Two cuts across the coverslip were made to form a transient tear in the plasma membranes of the cells to permit dye transfer through gap junctions. Cells were incubated with the dye for 20 minutes, then fixed and examined by fluorescent microscopy. For quantitative analysis the extent of dye transfer was estimated by counting the number of LY and RD labeled cells in the microscopic field and graphed. Three primaquine (PQ) analogs and mefloquine (MQ) blocked dye transfer significantly in comparison to the untreated control cells. However, PQ1 and MQ were the most potent blocker of the gap junction passage of the lucifer yellow dye as there was hardly any passage of the dye in cells treated with these two anti-malarial drugs. PQ3 shows inhibitory activity of about 20% as compared with the control. PQ3 is useful as a drug having reduced gap junction inhibitory activity. The gap junction activity of other compounds of the invention may be tested as described herein without the use of undue experimentation.

Methods Used in the Gap Junction Studies

Cell Culture: Murine hippocampal HT22 cells are cultured in DMEM (high glucose), supplemented with 10% fetal bovine serum and 50 µg/ml gentamicin, 0.05 units/ml penicillin, 50 µg/ml streptomycin, pH 7.4, at 37° C. in an atmosphere of 95% air and 5% $CO_2$. HT22 cells have endogenous Cx50 as their major gap junction protein. This is a common neural form of gap junction.

Gap junction Activity Assay: Gap junction activity is measured by the scrape load/dye transfer assay. HT22 cells are grown to 80% confluency then rinsed in fresh media and, in some cases, exposed to 100 µM hydrogen peroxide as an oxidative stress or 500 µM to induce apoptosis. After treatments, cells are rinsed in PBS then 2.5 µl of both 1% Lucifer Yellow and 0.75% rhodamine dextrin are added to the center of the coverslips and two cuts are made crossing each other and passing through the dye. After 1 min the cells are rinsed in PBS and the dye allowed to pass from cell to cell for an additional 10 min. Cells are then fixed in 2.5% paraformaldehyde and further rinsed in PBS. Dye transfer is evaluated by counting the number of cells taking up the Lucifer Yellow with damaged cells subtracted (those labeled with rhodamine dextrin), using a Nikon C1 confocal microscope. Four points are counted for each slide from 6 experiments and expressed as mean+/−S.E., $p<0.05$ as significant.

Western blot and immunoprecipitations: In some cases apoptosis is determined by measurement of active caspase-3 using specific active caspase-3 antisera. Cells are collected and lysed on ice with cell lysis buffer: 20 mM Tris-HCl, pH 78.5, 0.5 mM EDTA, 0.5 mM EGTA, 0.5% Triton X-100, 0.1% protease inhibitor cocktail, 5 mM NaFl, and 2 mM PMSF. After centrifugation at 12,000×g for 20 min, the supernatants are collected and used as whole cell extracts. Western blots, immunoprecipitation of caspase-3 and scanning and quantitation of blots are performed as previously reported (Lin, et al, J. Biol. Chem., (2005), 280:13682-13693.).

Caspase-3 Assays: Apoptosis is measured by quantitation of active caspase-3, a common protein which is activated during apoptosis in neural cells. In some cases the active caspase-3 protein is measured on Western blots using mouse anti-active caspase-3 which is commercially available. For caspase-3 immunocytology, HT22 cells are grown in Delta T dishes to 50% confluency and treated with either primaquine analogs or hydrogen peroxide and varying concentration doses for varying times. Cells are then fixed with paraformaldehyde and treated with anti-active caspase-3 primary antisera and Alexa fluor 568 secondary antisera. Cells are examined under a confocal microscope and number of labeled cells/50 cells counted and expressed as percent of cells in apoptosis.

EXPERIMENT FOUR

Anti-tumor Studies

Cancer in part is caused by the disruption in cell's homeostasis, affecting its ability to respond to extracellular signals, triggering some intracellular events which affect the gap junctional intercellular communication (GJIC). Gap junctions (GJ) are dynamic intercellular plasma membrane channels allowing the passage of small molecules (<1 KD) between adjacent cells. They are formed by the interaction of two hemichannels (connexon) in the adjacent cells, which, in turn are made of six subunits of connexin (Cx) proteins. The structure of connexins includes four hydrophobic membrane-spanning domains, two extracellular loops, one cytoplasmic loop, and an amino and carboxyl terminus in the cytoplasm. GJ are involved in tissue homeostasis, cell proliferation and differentiation, and the regulation of embryonic development and growth. Presently, 21 connexin genes have been identified in mammalian cells and three connexins, Cx43, Cx32 and Cx26 have been detected in normal breast tissue. Cx43 is the predominant form and detected mostly in myoepithelial cells. Cancer cells have reduced or altered GJIC capacity. Restoring GJIC is linked to drug sensitivity and reduction of tumorigenicity. Increasing gap junction activity or enhancing GJIC in tumor cells provides the targets to enhance anti-neoplastic therapies.

Compounds of the invention were studied by computational docking with the gap junction proteins (connexins) using Autodock computational docking software (Goodsell, D. S. and Olson, A. J. 1990. Automated docking of substrates to proteins by simulated annealing. Proteins: Structure, Function, and Genetics 8: 195-202; Morris, G. M., Goodsell, D. S., Huey, R. and Olson, A. J., 1996. Distributed automated docking of flexible ligands to proteins: parallel applications of AutoDock 2.4. *J. Computer-Aided Molecular Design* 10: 293-304; Morris, G. M., Goodsell, D. S., Halliday, R. S., Huey, R., Hart, W. E., Belew, R. K., Olson, A. J. 1998. Automated docking using Lamarckian genetic algorithm and an empirical binding free energy function. *J. Comp. Chem.* 19: 1639-1662). Compounds were bound to the inert core of the hexameric hemichannel of gap junctions. The efficacy of the compounds of an embodiment of the invention was tested by determining their effect on GJIC in human breast cancer cells as an exemplary system.

Out of PQ1-5 compounds tested, PQ1 shows the highest affinity to bind with the connexins. Scrape load dye/transfer technique is used to measure the GJIC. Previous studies show that restoration of GJIC prevents cancer formation. Cancer formation is checked by preventing cell proliferation and growth thereby leading to cell death. Cancer cells are characterized by abnormal cell growth and proliferation than normal cells.

Cancer cells do not undergo apoptosis at the same rate as normal cells. Apoptosis is programmed cell death causing cell shrinkage, blebbing from the surface, condensation of the chromatin, and changes in cell surface molecules to ensure the phagocytosis of the apoptotic cells. Many cancer therapeutic agents exert their effect through initiation of apoptosis. Apoptosis is induced via stimulation of different cell surface receptors along with caspase activation. Signals leading to the activation of intracellular cysteine proteases play a pivotal role in the execution of apoptosis.

Figure 3:
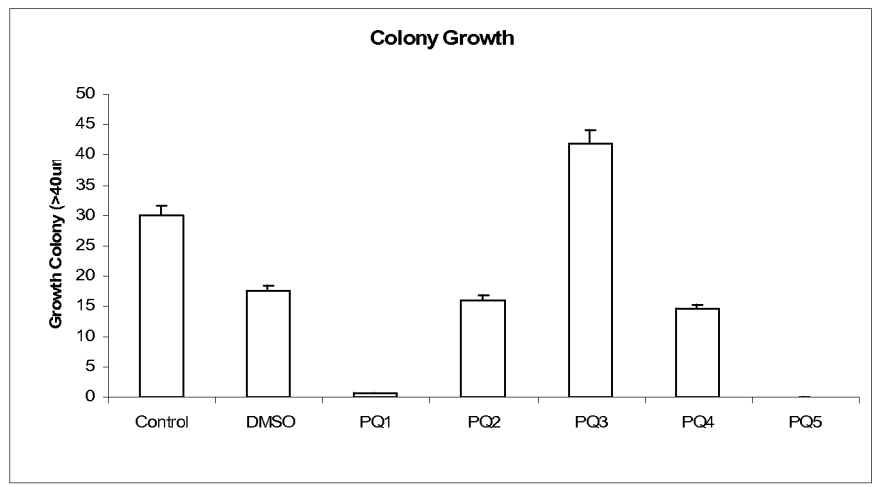
FIG. 3 shows MDA-MB-453 and T47D colony growth for PQ1-5 and DMSO, as well as a control.
Figure 3:
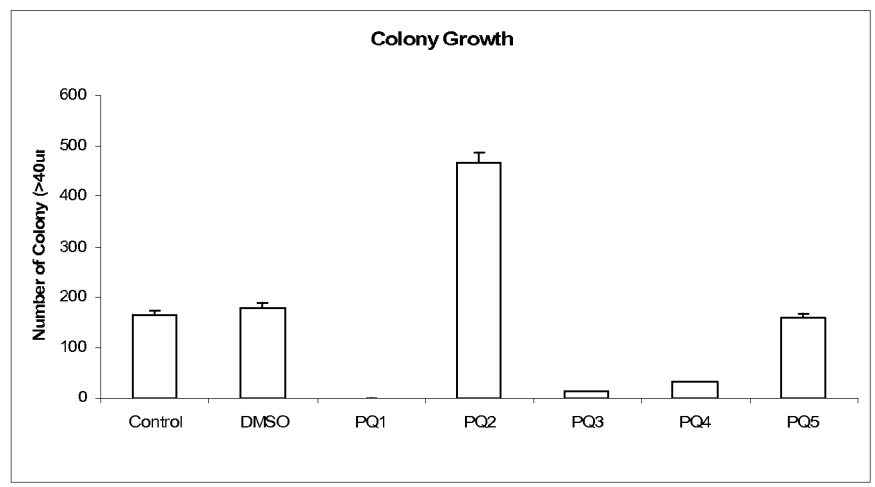
Figure 7:
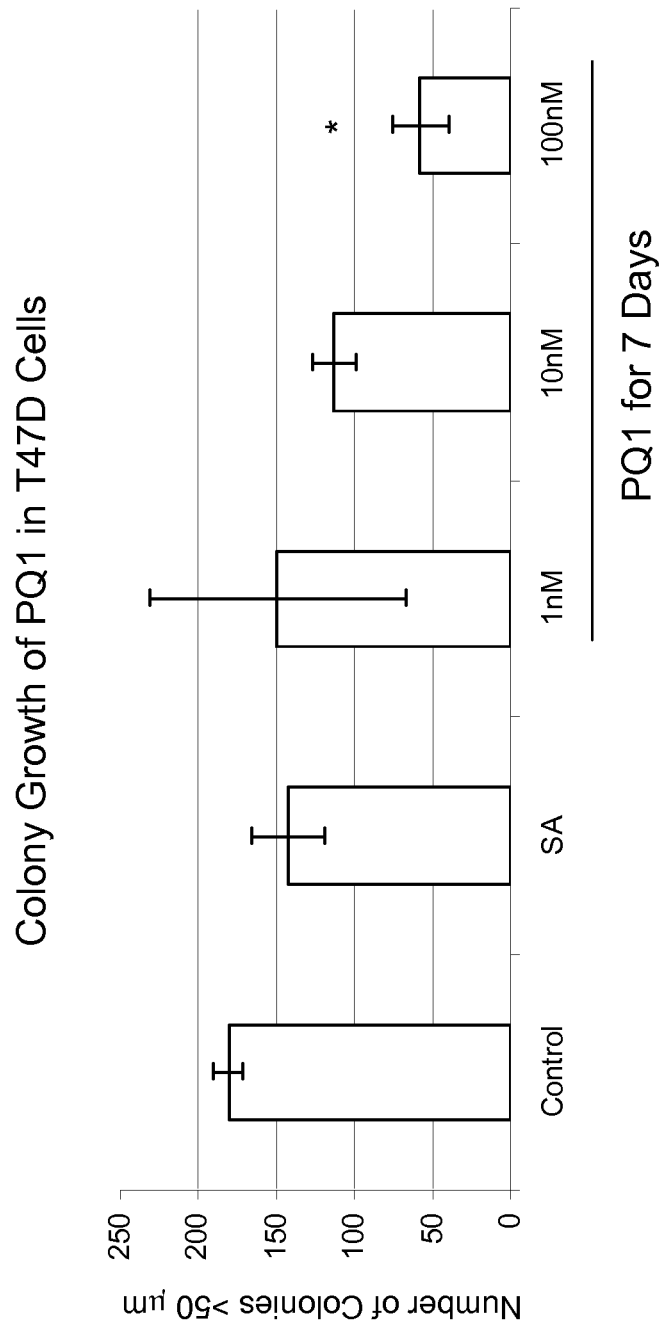
FIG. 7 shows colony growth of PQ1 in T47D cells.
Figure 8:
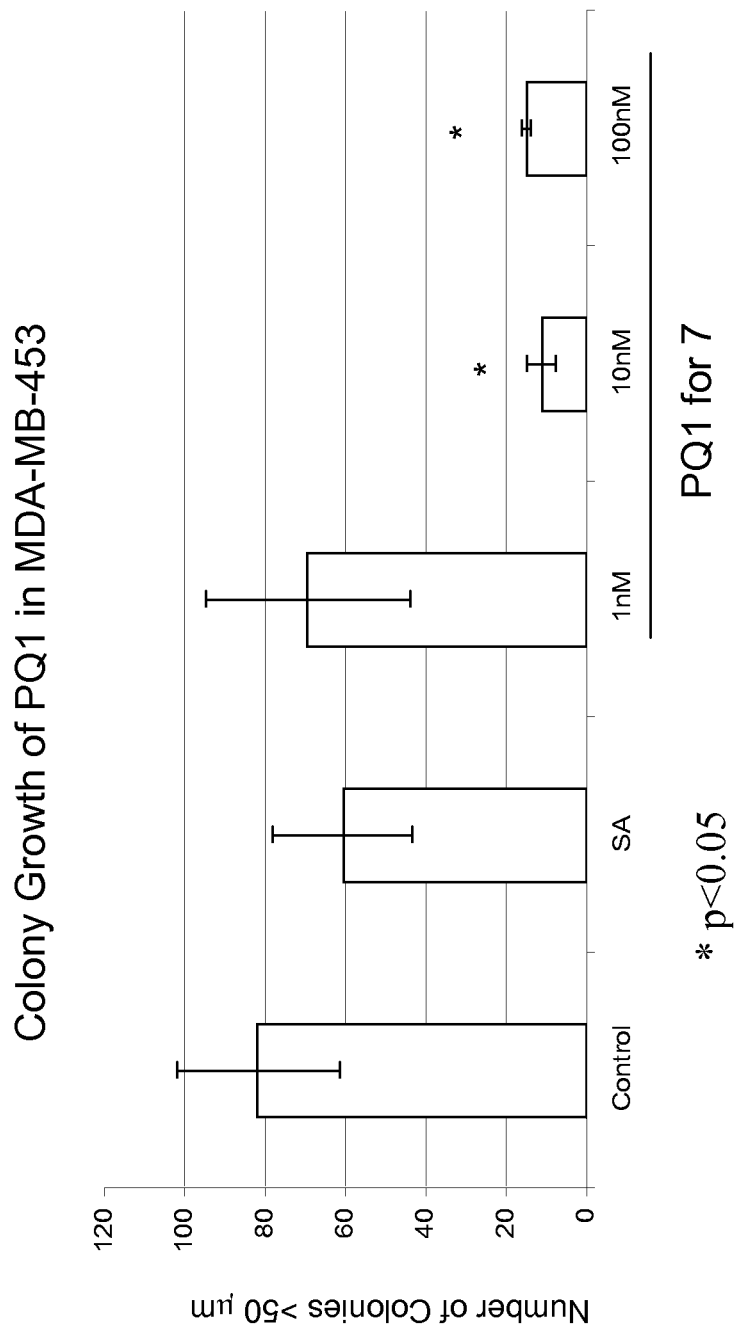
FIG. 8 shows colony growth of PQ1 in MDA-MB-453 cells.

FIG. 3 shows MDA-MB-453 and T47D colony growth for PQ1-5 and DMSO, as well as a control. FIG. 3(A) MDA-MB-453 and (B) T47D human breast cancer cells were treated with 10 µM of various quinolines for 7 days. Base agar plates were prepared containing 0.8% agar and 0.4% agar in Ham's F12. Cells ($5\times10^4$ cells/33 mm well) were suspended in 100 µl of Ham's F12 with 0.4% agar and plated. These plates were maintained at 37° C. for 7 days and examined for the presence of colonies. Individual colonies of 40 µm or greater were examined. The results demonstrated that PQ1 alone showed approximately 80-95% growth attenuation in both breast cancer cell lines compared to control. Additionally, PQ5 completely inhibited MDA-MB-453 colony growth. PQ3 and PQ4 have an inhibitory effect on T47D colony growth. However, PQ3 caused a 2.3-fold increase in colony growth in MDA-MB-453 cells and PQ2 caused a 2.6-fold increase in T47D colony growth compared to DMSO. FIGS. 7 and 8 show MDA-MB-453 and T47D colony growth for various concentrations of PQ1 and SA tested for 7 days. The procedures are generally as described above. The cell colony growth decreased using 10 and 100 nM PQ1 for both cell types.

Figure 4:
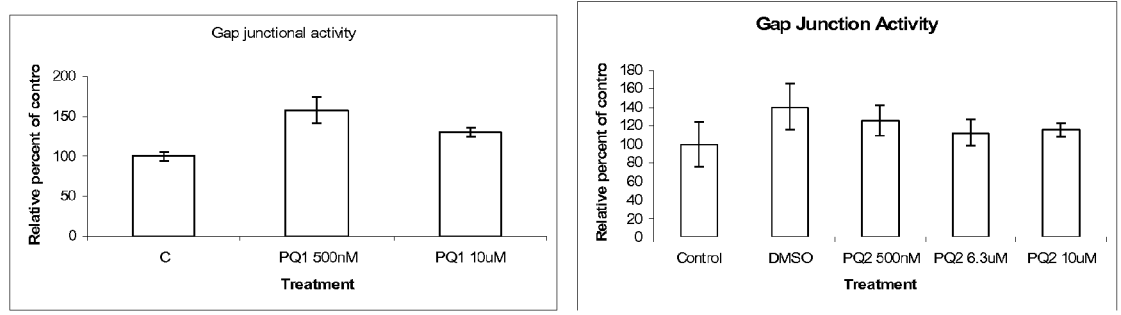
FIG. 4 shows gap junction activity using flow cytometry of dye coupling in human breast cancer cell lines.
Figure 4:
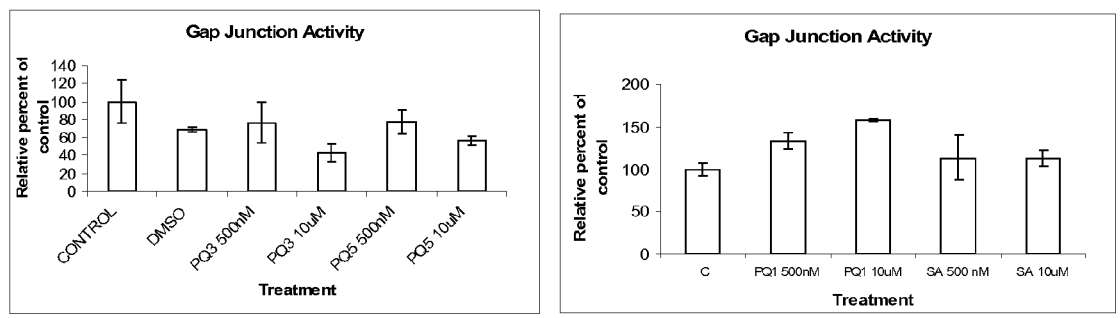

FIG. 4 shows that PQ1 has a tremendous effect on the GJIC in cells tested. The effect of PQ1 on these cancer cells showed a 20-50% increase in GJIC, suggesting the gain of GJIC in cancer cells plays a critical role in the anti-tumor treatment (FIG. 4). FIG. 4(A) MDA-MB-453 and (B) T47D cells were treated with low (500 nM) and high (10 μM) concentrations of PQs for 24 hours. Monolayers of acceptor cell population were grown on 25-cm flasks in the presence of Vibrant DiD. Vybrant DiD in acceptor cells is not able to pass through the gap junctions because of its hydrophobic property. Single cell suspensions of donor treated cells were prepared, labeled with 0.05 μg/ml calcein-AM, incubated at 37 C for 5 minutes. Quantification of dye coupling between the donor and acceptor cells was assessed by dual-excitation flow cytometry. The results demonstrated that 500 nM of PQ1 caused a 1.5-fold increase of gap junction activity compared to control; however, PQ2 has no significant effect on gap junction activity in MDA-MB-453 cells. Cells treated with 10 μM PQ3 have approximately 40-50% decrease in gap junction activity compared control or DMSO. Thus, these data provide evidence that increased or decreased gap junction directly affects cancer colony growth.

Figure 10:
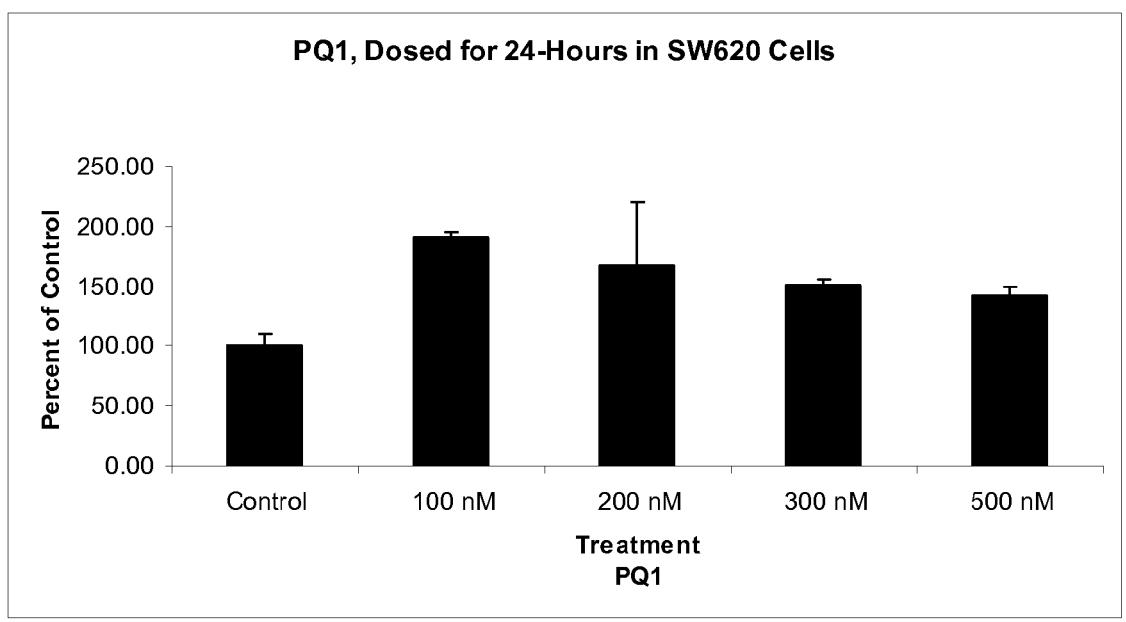
FIG. 10 shows the effect of PQ1 on gap junction activity in SW620 colon cancer cells.
Figure 11:
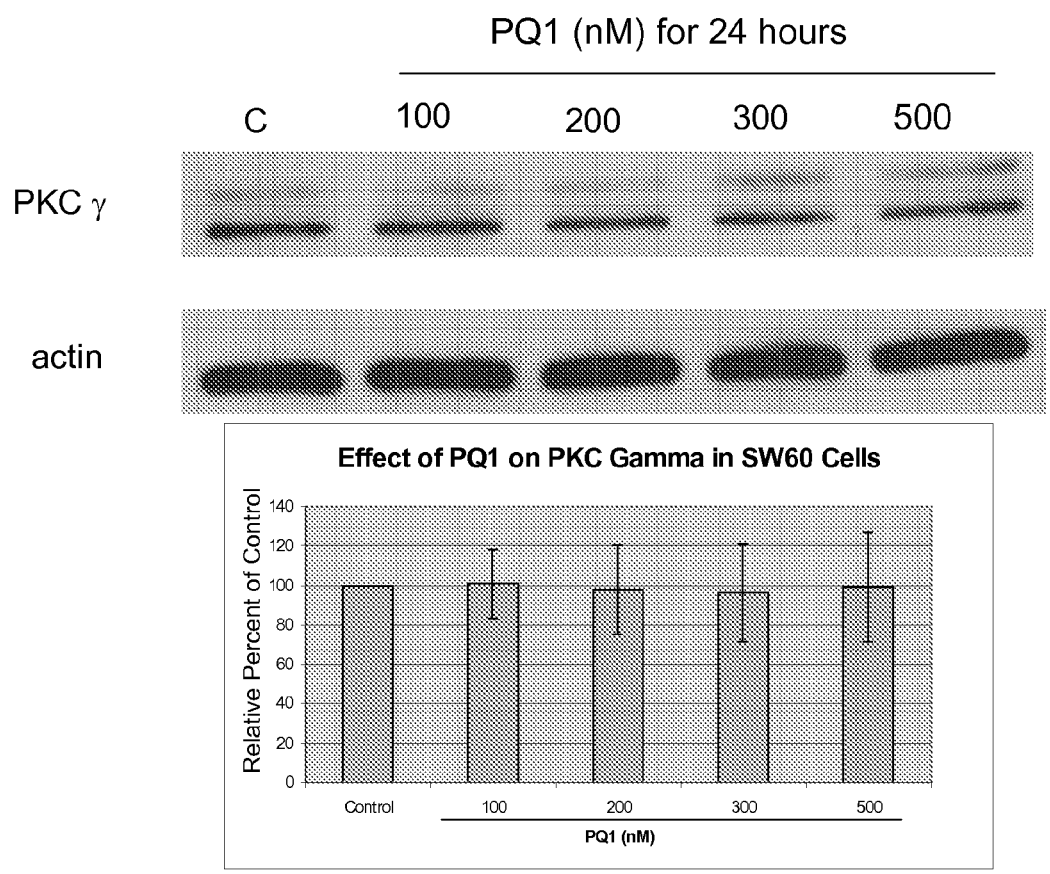
FIG. 11 shows the effect of PQ1 on the expression of PKCγ.
Figure 12:
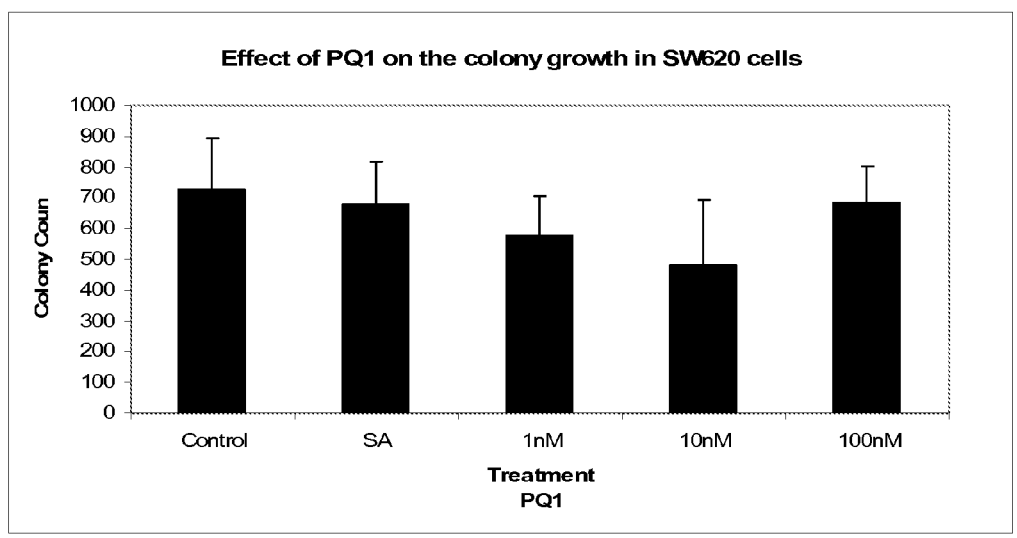
FIG. 12 shows the effect of PQ1 on colony growth of SW620 colon cancer cells with various concentrations of PQ1.
Figure 13:
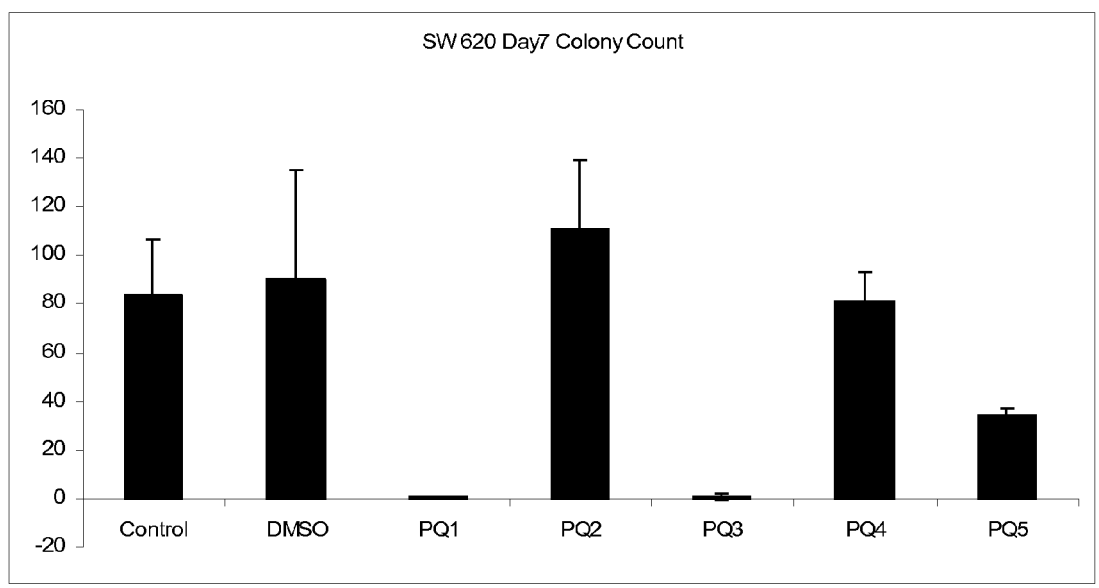
FIG. 13 shows the effect of PQ1 on colony growth of SW620 colon cancer cells with 10 uM PQ1 and other compounds.

Saez et al. demonstrated that increased in GJIC is directly related to the anti-tumor effect in human mammary cancer cell line (JCB 89, 2003). However, PQ3 has an opposite effect on mammary cancer cell lines. PQ3 alone exhibited approximately 2.3-fold increase in a colony growth assay and caused a 50% decrease in GJIC. A summary of PQ-mediated GJIC activity and colony growth in breast and colon cancer cells is presented in Tables 1, 2, and 3, as well as FIGS. 10-13. In FIG. 10, SW620 cells were dosed for 24 hours with PQ1 at 100, 200, 300, and 500 nM. The gap junction activity was measured as a percent of control, as previously described. It was seen that all concentrations on PQ1 increased the gap junction activity in SW620 colon cancer cells as compared to the control. In FIG. 11, the effect of PQ1 on the expression of PKCγ was studied at concentrations of 100, 200, 300 and 500 nM PQ1 for 24 hours. It is seen in FIG. 11 that PQ1 has no effect on the expression of PKCγ at the levels tested. In FIGS. 12 and 13, the effect of PQ1 on the colony growth of SW620 colon cancer cells was measured with 1-100 nM PQ1 (FIG. 12) and 10 uM PQ1 (FIG. 13). It can be seen that PQ1 has no effect on the colony growth in SW620 at the levels tested in FIG. 12, but completely inhibits SW620 at 10 uM. FIG. 13 also shows the colony growth effect of PQ2-PQ5.

Figure 9:
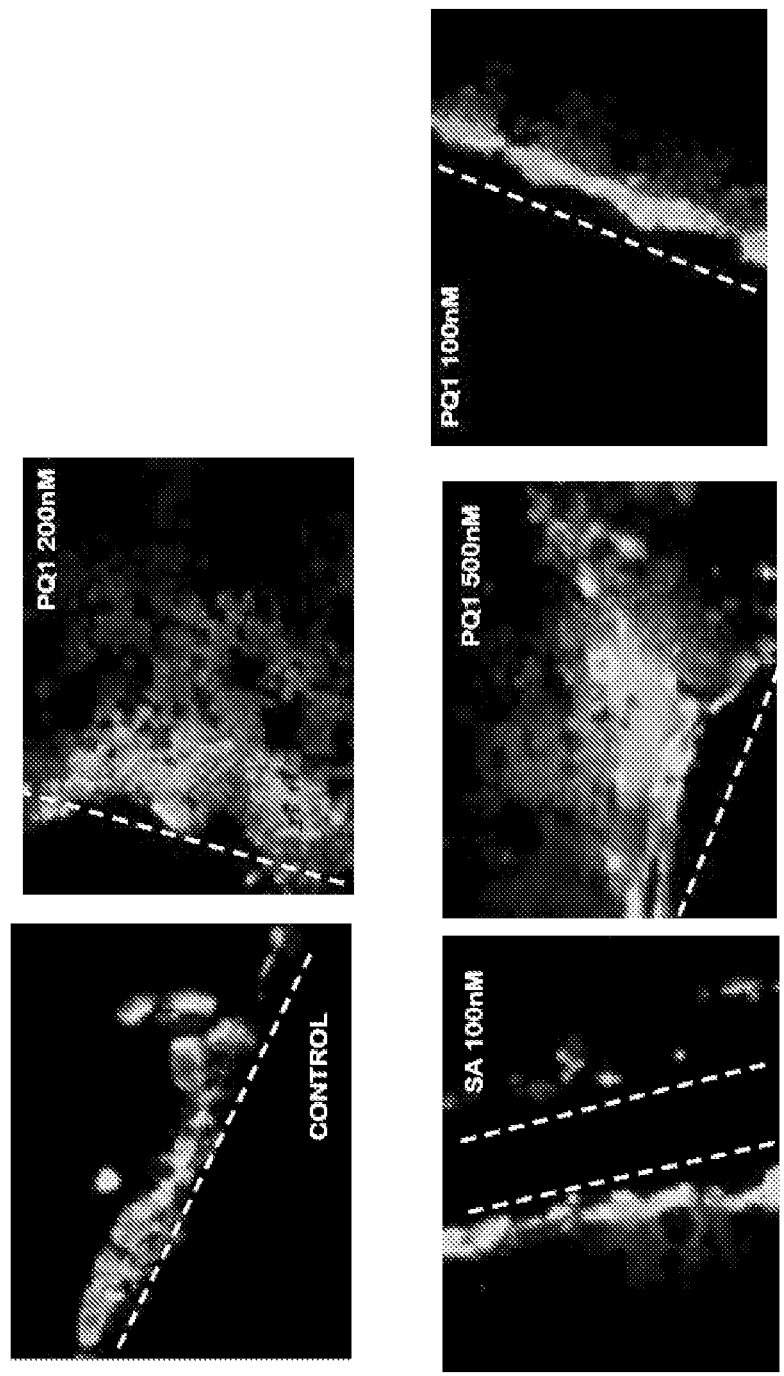
FIG. 9 shows results from scrape load dye/transfer with T47D cells

In the presence of 200 and 500 nM of PQ1 for 40 minutes, a significant increase in the gap junctional activity in T47D cells was seen (FIG. 9). In the experiments for FIG. 9, T47D cells were dosed with 100, 200 and 400 nM of PQ1 for 40 minutes. Lucifer yellow, a gap junctional permeable dye, was used to measure the GJIC. Rhodamine dextran was used as a control. The dotted line in FIG. 9 indicates the line of cut. This increase could be due to the interaction between the PQ1 and the connexin proteins which leads to the opening of the gap junction channel. PQ1 exerted no effect on the cell morphology of T47D cells (data not shown).

Figure 5:
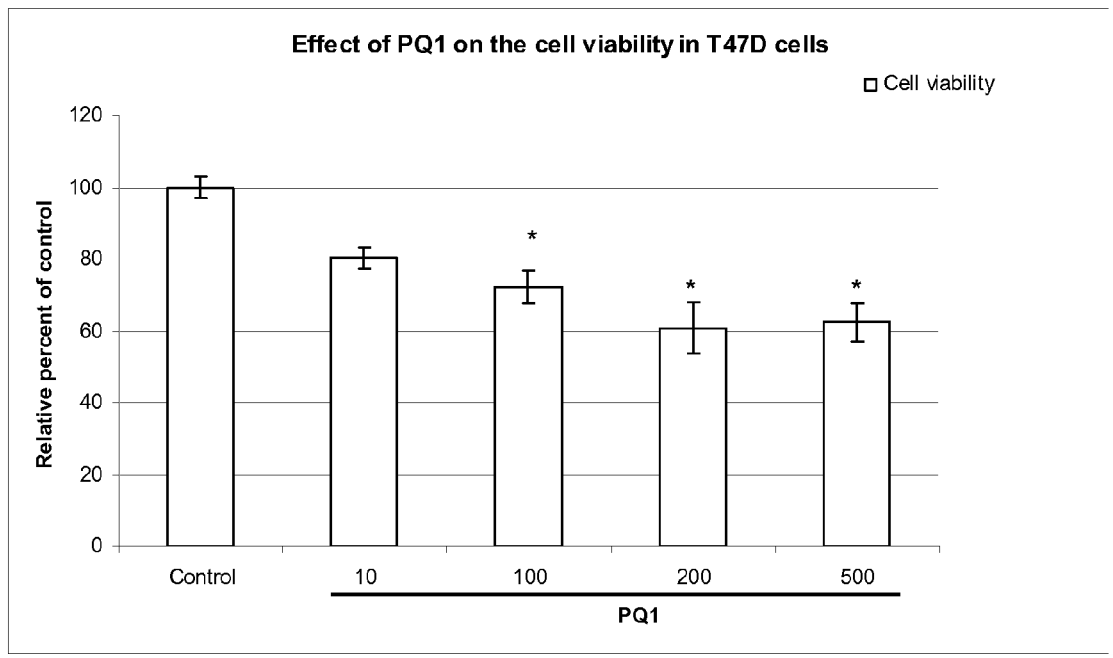
FIG. 5 is a MTT assay showing the effect of PQ1 compound on the cell viability in T47D cells.

PQ1 showed a 40% decrease in the cell proliferation in T47D cells. This effect was seen at 200 nM of PQ1 for 24 hours (FIG. 5). There was no effect seen on the cell proliferation in transformed human mammary epithelial cells (HMEC, data not shown). This suggests that PQ1 affects the cell viability of the cancerous cells without affecting the growth of normal cells.

Figure 6:
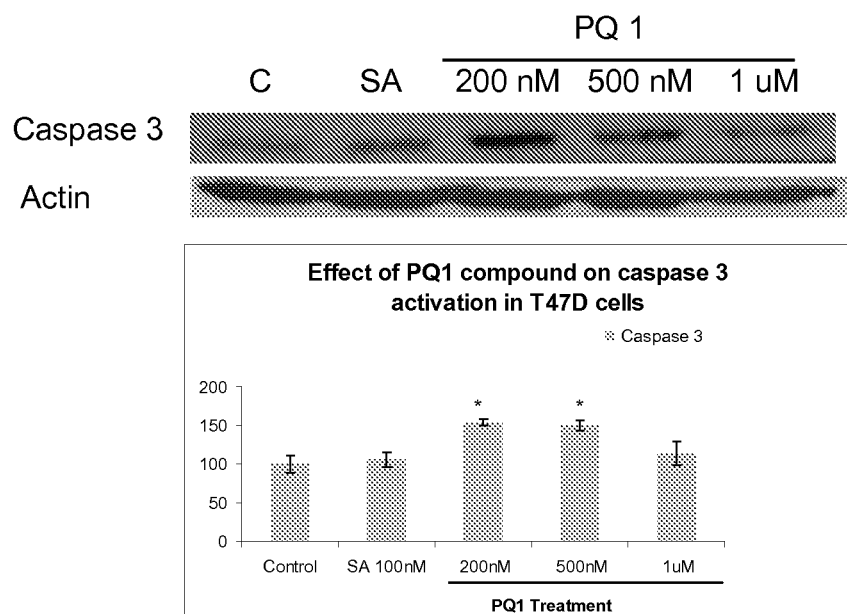
FIG. 6 shows PQ1 on the activation of caspase 3 in T47D cells.

The expression of caspases in the presence of PQ1 in T47D cells was studied. A significant 50% increase in the expression of active caspase 3 at 200 and 500 nM of PQ1 in T47D cells was found (FIG. 6).

Methods Used in Tumor Studies

Scrape load dye transfer technique (SL/DT): Lucifer yellow is an intensely fluorescent 4-aminophthalimide dye having low molecular weight (Mr 457.2) and passes from one cell to another through gap junctions only. Rhodamine dextran is a high molecular weight polymer (Mr 10,000) used as a control as passes only through injured plasma membrane. Cells were grown to 90% confluency on cover slips, dosed with PQ 1 for 40 minutes. The 2.5 μl of 1% (w/v) Lucifer yellow and 0.75% (w/v) of Rhodamine dextran was mixed and added in the center of the coverslip. Two cuts crossing each other in the center of the coverslip were made. After three minutes, cells were washed with PBS and incubated at 37° C. in tissue culture media for 20 minutes. Cells were fixed and mounted on a slide, sealed and visualized under a fluorescence microscope at 10× objective.

MTT assay: This assay is done to measure cell proliferation and viability. Yellow MTT (3-(4,5-Dimethylthiazol-2-yl)-2, 5-diphenyltetrazolium bromide, a tetrazole) is reduced to purple crystals, formazan in the mitochondria of living cells. A solubilization solution is added to dissolve the insoluble purple formazan product into a colored solution. The absorbance of this colored solution can be measured by a spectrophotometer. T47D cells (20,000) were grown in 96-well plate and dosed with 10, 100, 200, 500 nM of PQ1 compound in 100 μl of complete media for 24 hours. MTT (20 μl) was added to the cells and purple formazan crystals were observed after 90 minutes. A solubilization solution (0.35 N HCl) was added to dissolve the formazan and the absorbance was measured at 595 nm wavelength with a background wavelength 690 nm by a spectrophotometer.

Cell Morphology: T47D cells (1000 cells/ml) were seeded in a six-well plate for 24 hours. Next day, cells were dosed with varying concentrations of PQ1 for 24 hours. Cells were observed under a microscope before and after the experiment. No effect seen on the morphology of cells in the presence of PQ1.

Colony Growth Assay: T47D human breast cancer cells were treated with PQ1. Base agar plates were prepared containing 0.8% agar and 0.4% agar in Ham's F12. Cells ($5 \times 10^4$ cells/33 mm2 well) were suspended in 100 μl of Ham's F12 with 0.4% agar and plated. These plates were maintained at 37° C. for 7 days and examined for the presence of colonies. Individual colonies of 40 um or greater were examined.

Western Blot analysis: Cells were grown in RPMI media until they were 90% confluent in 75 cm2 flasks. Cells were dosed with 200, 500 nM of PQ1 for 24 hours. Cells were harvested with lysis buffer and centrifugated. Cell lysate was run on a 12% SDSpolyacrylamide gel electrophoresis (PAGE) and transferred to nitrocellulose membrane. Membrane was incubated with Caspase Antibody. Western blots were detected by enhanced chemiluminescence detection reagents.

As will be appreciated by one of ordinary skill in the art, the compounds and methods described here can be used for the inhibition of growth of other types of cancer, such as human prostate cancer, glioma, pancreatic cancer and other types of cancer.

The compounds used can be used to study drug-protein interactions, and can be used as known in the art to study in vivo effects, such as by using mouse, human and other animal studies.

TABLE 1

The effect of PQ compounds on gap junction intercellular communication in breast cancer cell lines

| Cell Line | PQ1 | PQ2 | PQ3 | PQ4 | PQ5 |
|---|---|---|---|---|---|
| MDA-MB-231 |  | Decrease | No effect | Decrease | No effect |
| MDA-MB-453 | Increase (500 nM) | No effect | Decrease | No effect | Decrease |
| MCF-7 | No effect | Decrease | Decrease | No effect | No effect |
| ZR75 | Decrease | No effect | No effect | No effect | No effect |
| T47D | Increase (500 nM) |  |  |  |  |

TABLE 2

The effect of PQ compounds on breast cancer cell colony growth

| Cell Line | PQ1 | PQ2 | PQ3 | PQ4 | PQ5 |
|---|---|---|---|---|---|
| MDA-MB-453 | Decrease | No effect | Increase | No effect | Decrease |
| T47D | Decrease | Increase | Decrease | Decrease | No effect |

TABLE 3

The effect of PQ compounds on gap junction intercellular communication in colon cancer cell lines

| Cell Line | PQ1 | PQ2 | PQ3 | PQ4 | PQ5 |
|---|---|---|---|---|---|
| HT29 | No effect | Increase | Increase | Increase | Increase |
| SW620 | Increase (300 nM) | Increase (6 uM) | Increase (500 nM) | No effect | Decrease (300 nM) |

EXPERIMENT FIVE

Antitumor Effect in Breast Cancer Cells

Figure 14:
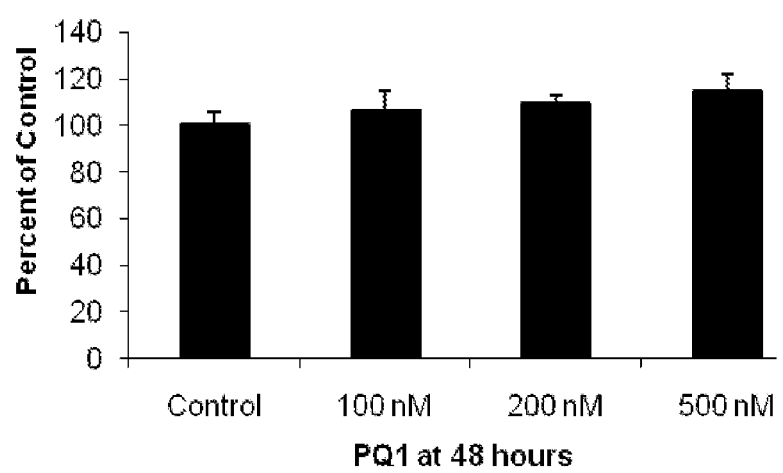
FIG. 14 shows the effect of PQ1 on transepithelial electrical resistance (TEER). T47D cells were treated with 0, 100, 200, and 500 nM PQ1 for 48 hours. TEER assay was performed as described herein. TEER values of each treatment in $K\Omega/cm^2$ were converted to relative percent of control.

Intercellular communication in many organs is maintained via GJIC. Several GJIC enhancers have been reported; however, an effective clinical drug targeting gap junction is not available at this time. The effect of PQ1 on the GJIC activity in T47D breast cancer cells was tested. The results demonstrated that 100, 200 and 500 nM of PQ1 show a significant increase in gap junction activity compared to controls, without PQ1 treatment and succinic acid, using scrape load/dye transfer assay (data not shown). Conversely, PQ1 has no effect on GJIC activity of human primary epithelial cells (MEC, normal cells) compared to its controls (data not shown). The distance of dye transfer from section cut to the farthest cells with dye was measured. A graphical presentation of three experiments indicates that 200 nM PQ1 causes an 8.5-fold increase in distance of dye transfer compared to control (data not shown). MECs have uniform uptake of Lucifer yellow. This is due to the existing high level of gap junction activity of these normal cells. Furthermore, 100, 200, or 500 nM of PQ1 has no significant effect on tight junction ion permeability by using transepithelial electric resistance (TEER) compared to control (FIG. 14). This suggests that PQ1 only affects gap junction and not tight junction. These results demonstrated that PQ1 is sufficient to cause an increase in GJIC activity in SL/DT assay.

Figure 15:
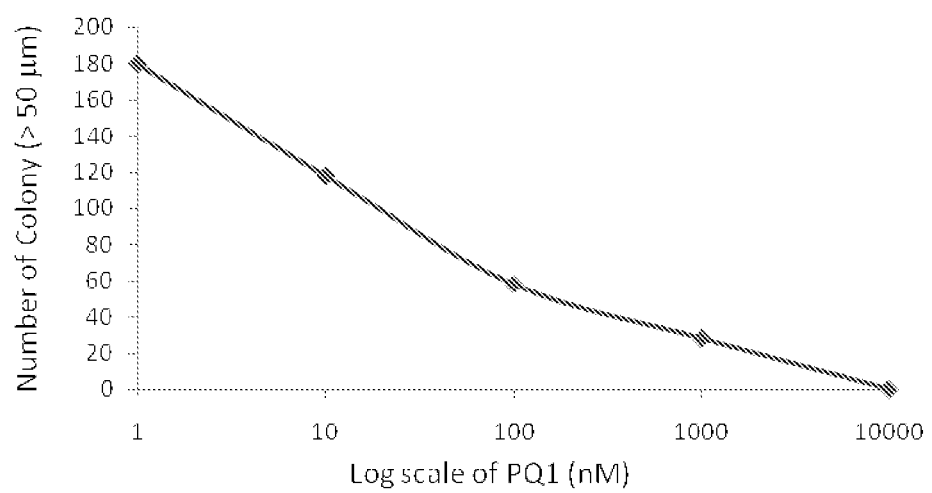
FIG. 15 shows the effect of Substituted Quinolines on T47D Cells. Base agar plates were prepared containing 0.8% agar and 0.4% agar in Ham's F12. Cells ($5 \times 10^4$ cells/33 $mm^2$ well) were suspended in 100 µl of Ham's F12 with 0.4% agar and plated. These plates were maintained at 37° C. for 7 days and examined for the presence of colonies. Individual colonies of 50 µm or greater were examined. T47D cells were treated with 1, 10 and 100 nM PQ1 and SA (succinic acid) as a solvent control. Individual colonies of 50 µm or greater were examined. Statistical significance, *p<0.05, of at least three experiments

Various oncogenes (e.g. ras, raf, neu, src, mos) down-regulate GJIC while several tumor suppressor genes can up-regulate GJIC. The effect of PQ1-upregulated gap junction activity in T47D colony growth formation was studied. Cells were grown in soft agar to assess their capacity for anchorage-independent growth, which is a key feature of cell transformation due to the importance of cell-cell and cell-matrix based tumor suppression. MEC and T47D cells were treated with 10, 100, 1000, and 10000 nM PQ1 for 7 days. A graphical presentation of three experiment results is presented in log scale of PQ1 concentration. The effect of PQ1 on T47D cells showed a significant inhibition of T47D cell colony growth compared to control (FIG. 15). A 100 nM PQ1 inhibits 66% of colony growth compared to controls, without PQ1 treatment or 100 nM succinic acid. Interestingly, the same concentration (100 nM PQ1) has no effect on MECs (data not shown). This suggests that 100 nM PQ1 can cause an increase in GJIC activity and subsequently can decrease colony growth of T47D cells.

Figure 16:
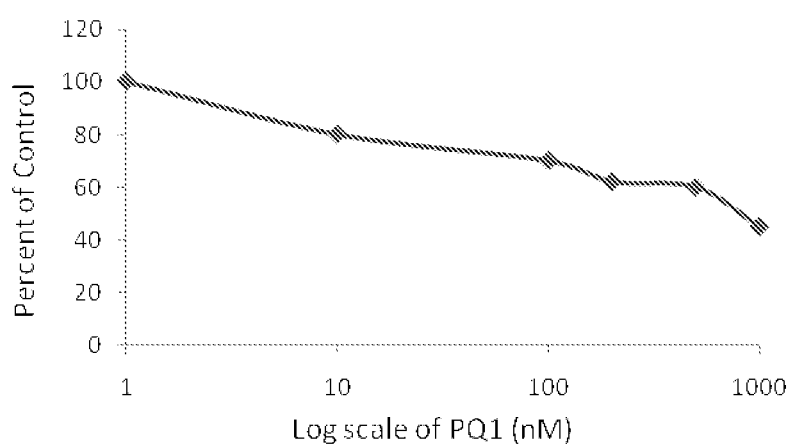
FIG. 16 shows the effect of PQ1 on Cell Viability. T47D breast cancer cells were treated with various concentrations of PQ1 for 24 hours. MTT assay was performed with adherent cell cultures using a culture medium free of phenol red and of serum. Solution containing MTT was metabolized by the cells (incubation period 3 hours). After solubilization of the MTT crystals with the solubilization solution MTT, the amount of dye was measured spectrophotometrically at 540 nm.

The cytotoxicity of PQ1 in MEC and T47D cells using MTT assay was also determined. Cells were treated with 10, 100, 200, and 500 nM PQ1 for 24 hours. MTT assay was performed according to the manufacture's recommendations. A 200 nM PQ1 has 67% cell viability compared to controls (FIG. 16). Treatments of 100 and 200 nM PQ1 have 95% and 103% MEC cell viability compared to control. However, both MEC and T47D cells decrease cell viability to 50% and 65% at 1 $\mu$M PQ1, respectively. Thus, 100-200 nM of PQ1 is sufficient to enhance GJIC activity.

Figure 17:
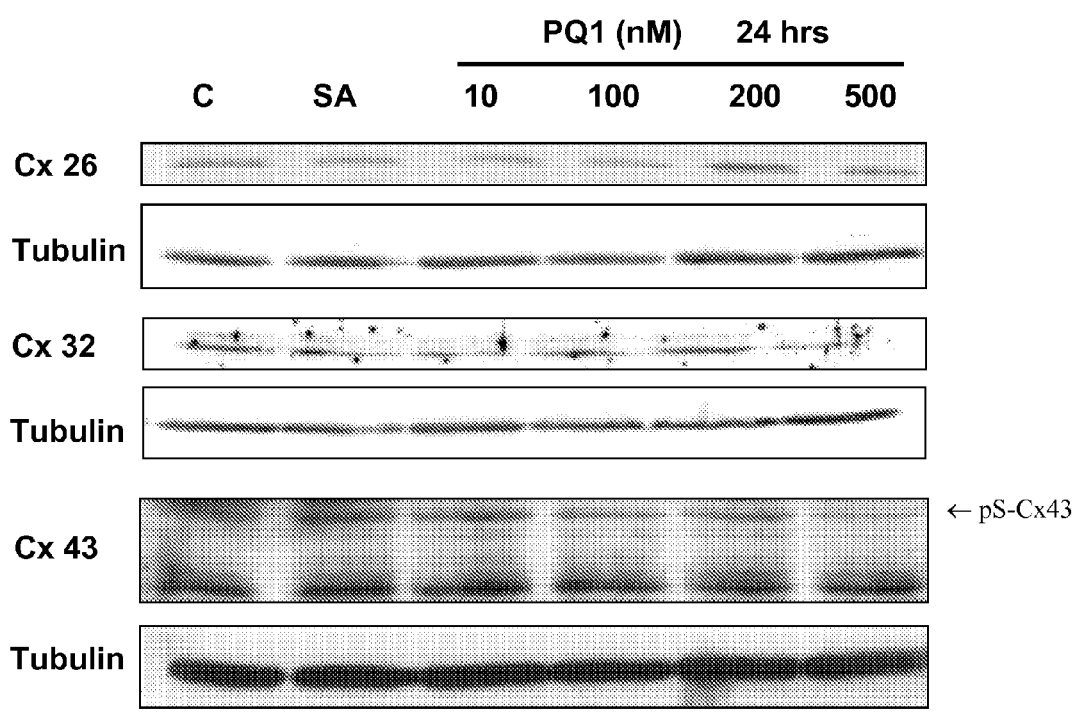
FIG. 17 shows the effect of PQ1 on the expression of different connexins in T47D cells. T47D cells were dosed with PQ1 for 24 hours. The Western blot analysis was performed as described in Materials and Methods. Whole cell extract was analyzed for Cx 43, Cx32, and Cx26. Experiment was performed at least three times.

Furthermore, whole cell extract of PQ1 treatment was analyzed for the changes in gap junctional proteins, connexins. Cells were treated with 10, 100, 200, and 500 nM PQ1 for 24 hours. Western blot analysis was performed against Cx26, Cx32, and Cx43 (FIG. 17). The results show that PQ1 has no effect on Cx26, Cx32, and Cx43 expression. Interestingly, a decrease in phosphorylated Cx43 was observed in 500 nM PQ1 treatment of T47D cells. Anti-tubulin was used as a loading control. These results suggest that PQ1 does not affect the expression of connexins but directly causes a decrease in phosphorylation of connexin.

Figure 18:
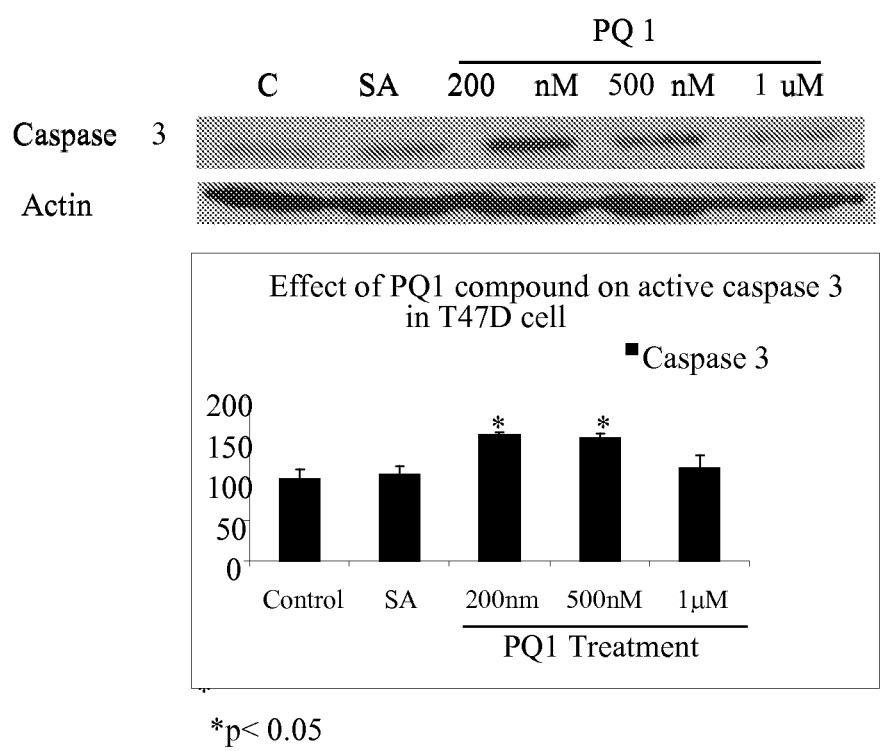
FIG. 18 shows the effect of PQ1 on Active Caspase 3. T47D cells were treated with 0, 200 nM, 500 nM and 1 µM PQ1 for 24 hours. Treatment with succinic acid was used as control. Western blot analysis was performed. Nitrocellulose membrane was blotted with the active form of caspase 3 antibodies (16 kDa). Actin acts as loading control. Graphical presentation of three experiments are presented with statistical significance, p<0.05.

Mitochondrial damage in treatment of PQ1 was observed using electron microscopy (data not shown), suggesting that these cells are under stress and apoptotic conditions. The effect of PQ1 on apoptosis was further examined by detecting the active form of caspase 3. T47D cells were treated with 100, 500, and 1000 nM PQ1 for 24 hours. Western blot analysis was performed using active form of caspase 3 antibodies. A 200 nM PQ1 causes 1.5-fold increase of active caspase 3 compared to control (FIG. 18). However, a decrease of caspase is observed in higher concentrations, a common effect in apoptotic protein expression. This is due to the cytotoxicity response of the cells.

Figure 19:
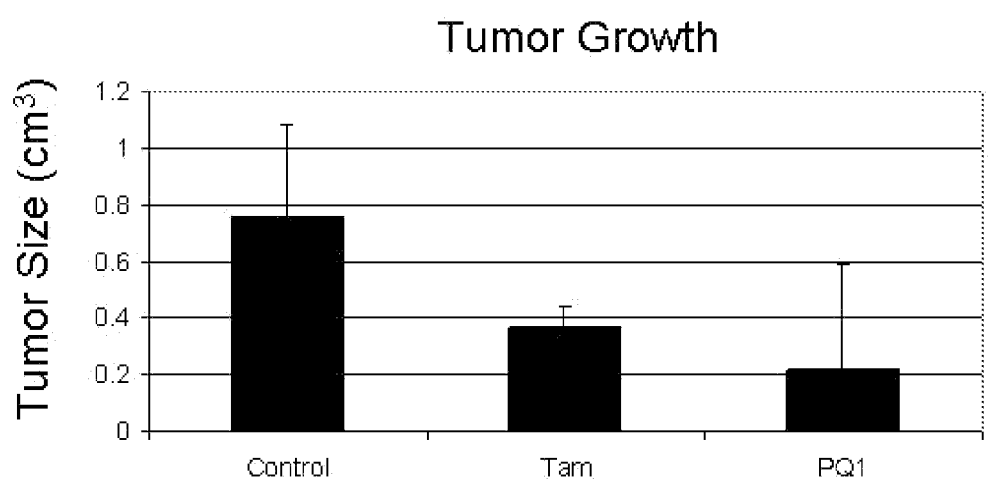
FIG. 19 shows xenograft Tumor Growth of T47D Cells in Nu/Nu Mice. Mice were inoculated with 17β-estradiol (1.7 mg/pellet) before the injection of $1 \times 10^7$ T47D cells subcutaneously into the inguinal region of mammary fat pad. Animals received treatment at 1 µM PQ1 or 10 µM tamoxifen. The results after 6 days of injection show a decrease in tumor growth of PQ1-treated animals compared to control or tamoxifen.

The anti-tumor effect of PQ1 was also observed in animal model. Nu/Nu mice were inoculated with estradiol-17β (1.7 mg/pellet) before the injection of 1×10$^7$ T47D breast cancer cells subcutaneously into inguinal region of mammary fat pad. The results of xenograft tumors demonstrated a decrease in tumor size with PQ1-treated group compared to control at Day 2; however, all three control animals along with a tamoxifen-treated animal (used for comparison of efficacy) were euthanized after Day 6 due to the systemic abnormality observed by attending veterinarian. The results show a 70% decrease of tumor growth with PQ1 treatment compared to control at Day 6 after one injection (FIG. 19).

It is shown that an increase in GJIC activity in T47D cells can cause a decrease in cell growth (FIG. 15). Interestingly, PQ1 only affects T47D breast cancer cells and not normal mammary epithelial cells. Through the passage of signaling molecules, GJIC contributes to the regulation of cell proliferation, differentiation, cell death, and homeostatic maintenance. Numerous studies clearly show that altered GJIC is involved in cell cycle progression. In most cell types, GJIC is reduced in the late G1, S and M phases [Ruch 1994]. The specific cell cycle state in which GJIC and/or connexin expression are modified, however, depend on both the cell type and the nature of the connexin species being investigated. PQ1 has no effect on connexin expression; however, it causes an increase in phosphorylation of connexin (FIG. 17). Upregulation of GJIC activity is dependent on the unphosphorylated connexins. Thus the observation is consistent with the increase of GJIC activity and a decrease of phosphorylation of connexin 43 (FIG. 17).

To study the effect of PQ1 in tumor bearing mice, xenograft tumor of T47D cells was prepared. The results show a 70% decrease of tumor growth with PQ1 treatment compared to control at Day 6 after one injection (FIG. 19). The standard deviation of control and PQ1 groups is high since the number of animals per group for the study is not sufficient. However, the results provide evidence that PQ1 has an anti-tumor effect in animal model. The data clearly shows that PQ1 is an effective anticancer agent.

PQ1 specifically enhances GJIC activity and does not affect the transepithelial electrical resistance of T47D cells. An increase of PQ1-induced GJIC activity causes a significant decrease of colony cell growth; however, PQ1 has no effect on primary mammary epithelial cells. Since normal epithelial cells have well-regulated gap junction channels, the change of GJIC activity in these cells was not observed. The decrease of cell viability and colony cell growth is subsequently of PQ1-induced apoptosis as the result of upregulation of active caspase 3. Thus, PQ1 is the first known compound to enhance GJIC activity in T47D breast cancer cells and subsequently attenuate tumor growth of xenograft tumors in nu/nu mice.

Materials and Methods

Cell line and cell culture. T47D human breast cancer cell line was purchased from American Type Culture Collection (Manassas, Va.). Cells were grown in RPMI medium supplemented with 10% fetal bovine serum (Atlanta Biologicals, Lawrenceville, Ga.), 10% antibiotic-actinomycotic at 37° C. with 5% $CO_2$ in 75 $cm^2$ flasks.

Western Blot Analysis. Cells were grown in serum supplemented RPMI media until they were 90% confluent in 75 $cm^2$ flasks. Cells were kept in starving media containing phenol red-free DMEM with 5% charcoal dextran stripped serum, overnight. Cells were dosed with 0, 10, 100, 200 and 500 nM of PQ1 for 24 hours. Cells were washed three times with cold PBS and then were harvested using lysis buffer (20 mM Tris pH 7.5, 0.5 mM EDTA, 0.5 mM EGTA, 0.5% Triton X-100) with 1:1000 dilution of protease inhibitors (Sigma-Aldrich, Saint Louis, Mo.). Cell lysate was sonicated and centrifuged at 13,000 rpm for 30 minutes at 4° C. Twenty-five µg of whole cell extract was resolved by 10% SDS-polyacrylamide gel electrophoresis (PAGE) and transferred to nitrocellulose membrane (Midwest Scientific, Saint Louis, Mo.). Nitrocellulose membrane was blocked in 5% milk for an hour at room temperature and then incubated with monoclonal mouse PKC α, 1:500 (Santa Cruz Biotechnologies, Santa Cruz, Calif.), mouse Cx43, 1:500 (Fred Hutchinson, Seattle, Wash.), rabbit actin, 1:1,000 (Sigma-Aldrich, Saint Louis, Mo.). Western blots were detected by enhanced chemiluminescence detection reagents (Pierce, Rockford, Ill., USA).

Gap Junction Activity. For scrape load/dye transfer (SL/DT) assay, cells were grown to 90% confluency on cover slips, dosed with 10, 50, 100 and 200 nM of TCDD for 40 minutes. After that cells were washed three times with PBS. The 2.5 µl of 1% (w/v) Lucifer yellow and 0.75% (w/v) of Rhodamine dextran was mixed and added in the center of the coverslip. Two cuts crossing each other in the center of the coverslip were made. After three minutes, cells were washed three times with PBS and incubated at 37° C. in tissue culture media for 20 minutes. The cells were then washed with PBS three times and fixed in 2.5% paraformaldehyde for 10 minutes. Cells were mounted on a slide, sealed and visualized under a fluorescence microscope at 10× objective.

Measurement of transepithelial electrical resistance. Cells were grown to 100% confluency on a 12-well transwell (BD Biosciences, San Jose, Calif.) and treated with 0, 100, 200, and 500 nM PQ1 for 48 hours. Transepithelial electrical resistance (TEER) of the T47D monolayers was measured by a high-precision. Resulting voltages were recorded with the aid of a differential amplifier with a high input resistance. Data were corrected for well area (given in $\Omega \cdot cm^2$).

Colony Growth Using Soft Agar. Cells were treated with 0, 10, 100, 200 and 500 nM PQ1 for 7 days. Base agar plates were prepared containing 0.8% agar and 0.4% agar in Ham's F12. Cells ($5 \times 10^4$ cells/33 $mm^2$ well) were suspended in 100 µl of Ham's F12 with 0.4% agar and plated. These plates were maintained at 37° C. for 7 days and examined for the presence of colonies. Individual colonies of 50 µm or greater were examined.

MTT assay. MTT (3-(4,5-dimethyl thiazol-2-yl)-2,5-diphenyl tetrazolium bromide) assay was performed with adherent cell cultures using a culture medium free of phenol red and of serum. Solution containing MTT was metabolized by the cells (incubation period 3 hours). MTT is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. The more viable cells will be presented in a well, the more formazan dye will be produced. After solubilization of the MTT crystals with the solubilization solution MTT, the amount of dye will be measured spectrophotometrically at 540 nm.

Xenograft Tumors of T47D cells in Nu/Nu Mice. Nu/Nu mice were ordered from The Jackson Laboratory. Mice were inoculated with estradiol-17β (1.7 mg/pellet) before the injection of $1 \times 10^7$ T47D breast cancer cells subcutaneously into inguinal region of mammary fat pad. Cell viability of T47D cells were performed prior to injection. The tumor size was measured in three dimensions with calipers every 2 days starting at Day 7. Mice were observed for any change in behavior, appearance or weight. When tumors reached 30-50 $mm^3$, three animals were randomly assigned to each treatment group. Animals were injected with 1 µM of PQ1 or 10 µM of tamoxifen and a single injection of treatment was set for 7 days and daily measurement of tumor size was recorded.

General Methods for Organic Synthesis. The synthesis of compounds used in these studies is described elsewhere herein. NMR spectra were obtained at 400 MHz for $^1H$ and 100 MHz for $^{13}C$ in $CDCl_3$, and reported in ppm. High-resolution Mass spectra were obtained from ESI spectrometers. ESI spectra were acquired on a LCT Premier (Waters Corp., Milford, Mass.) time of flight mass spectrometer. Satisfactory $^1H$ and $^{13}C$ NMR spectra and high-resolution mass spectra of compounds PQ1, PQ2, PQ3, PQ4, PQ5, and 10 were obtained (data not shown).

Statistical analysis: The level of significance (see * in figure legends) was considered at $p<0.05$ using Student's t test analysis. All data are presented as mean±S.D. of at least three independent experiments from different batches of cultures.

EXPERIMENT SIX

Protection of Retinal Cells from Apoptosis

As described above, cells which become ischemic will pass an apoptotic signal to adjacent cells, resulting in the spread of damage. This occurs through open gap junctions. In this experiment, cobalt chloride was used to induce a chemical hypoxia/ischemia condition in a rat retinal neurosensory cell line, R28. $CoC_{12}$ has been shown to induce oxidative damage through the generation of reactive oxygen species (ROS) in a wide variety of cells and has been recently reported to cause degeneration of mammalian retinal photoreceptor cells. R28 cells offer a well-characterized population of precursors to multiple neuroretinal cell types to investigate ischemia-induced apoptosis.

Cell cultures. The rat retinal neurosensory R28 cells were cultured in DMEM (low glucose) (Invitrogen, CA) supplemented with 10% fetal bovine serum and 50 µg/ml gentamicin, 50 U/ml penicillin, 50 µg/ml streptomycin, pH 7.4, at 37° C. in an atmosphere of 95% air and 5% $CO_2$.

Cobalt chloride ($CoCl_2$) treatment-a chemical hypoxia model in R28 cells.

Approximately 70% confluent retinal R28 cells were pre-incubated with PQ1 (10 µM, 40 min), followed by $CoCl_2$ treatments at 100, 200 and 500 µM for different time periods in a cell culture chamber (5% $CO_2$, room air, 37° C.). Hypoxia induction was confirmed by testing the hypoxia-inducible factor 1-α (HIF1α) protein expression levels in nuclear extracts by Western blotting.

Gap junction activity assay. R28 cells were grown to 90% confluency on coverslips. They were treated with PQ1 at 10 µM for 40 min. A mixture of 1% each, in PBS, Lucifer yellow (LY) and Rhodamine Dextran (RD) (Molecular Probes, Eugene, Oreg.) were added to the cells at the center of the coverslip. Two cuts across the coverslip were made to form a transient tear in the plasma membranes of the cells to permit dye entry into cells. Cells were incubated with 2.5 µl of both of the dyes for 20 min, then fixed in 2.5% paraformaldehyde, washed in PBS and examined by fluorescent microscopy using a Nikon C1 confocal microscopy. For quantitation, the extent of dye transfer was calculated by counting the number of LY-labeled cells from the initial scrape with subtraction of RD-labeled cells, as a cell damage control, in the microscopic field. Four points per slide were photographed. The experiments were repeated six times, and data are means±SEM.

Nuclear extracts. Following treatments with PQ1 and/or CoCl2, R28 cells were scraped into cold phosphate-buffered saline, centrifuged and washed once in five packed cell volume equivalents of buffer A (10 mM Tris-HCl (pH 7.5), 1.5 mM MgCl2, mM KCl) freshly supplemented with 0.5 mM dithiothreitol, 1 mM sodium orthovanadate, 0.4 mM phenylmethylsulfonyl fluoride, and 10 µl/ml of protease inhibitor cocktail (Sigma # P8340). Cell pellets were resuspended in 2.5 packed cell volume equivalents of buffer A and incubated in a pre-chilled Dounce homogenizer on ice for 10 min followed by homogenization by 20 strokes with a type B pestle. Nuclei were pelleted by centrifugation at 10,000 g for 10 min, the supernatant was discarded and nuclei were resuspended in 3.5 packed nuclear equivalent volumes of buffer B (20 mM Tris-HCl (pH 7.5), 1.5 mM MgCl2, 0.42 M KCl, 20% (v/v) glycerol) freshly supplemented with 2 mM DTT, 1 mM sodium orthovanadate, 0.4 mM phenylmethylsulfonyl fluoride, and 10 µl/ml of protease inhibitor cocktail. The suspension was rotated at 4° C. for 30 min and centrifuged for 30 min at 14,000 rpm. The eluted nuclear proteins in the supernatant were collected and HIF1a protein levels were measured by Western blotting.

Western blot. Western blotting was performed as described previously. Anti-Cx43 was purchased from Fred Hutchinson cancer research center (# Cx43NT1), anti-HIF1a was purchased from Novus Biologicals (# NB100-105), and anti-caspase-3 (# 9661), phosphor-Cx43 (Ser368) (#3511S) were purchased from Cell Signaling Technology and anti-b-actin was purchased from Sigma (# A5441).

Apoptosis assay. Approximately 70% confluent R28Cells in 25 cm2 flasks were treated with PQ1 at 10 µM for 40 min followed by treatment with 500 µM CoCl2 for different time periods to induce apoptosis. After this, cells were harvested and stained with Annexin V-FITC and propidium iodide (PI) according to the manufacturer's protocol (BioVision # K101-100). Annexin V-FITC/PI binding was analyzed by flow cytometry using a BD FACSCalibur system and data was analyzed using the CellQuest software.

Statistical analyses. All analyses represent at least triplicate experiments. The statistical analysis employed here is the Student's t-test. The level of significance (*) was considered at $p \leq 0.05$. All data are means±SEM.

Docking and Synthesis of Primaquine 1 (PQ1)

Since selective inhibition of gap junction intercellular communication with small molecules can be used to prevent cells from death during ischemic stroke, computational docking methods were used to search for chemicals that bind to the Cx43 gap junction hemichannel, based upon the partial crystal structure. Primaquine (PQ1) analogs were synthesized as described herein. The succinic acid salt of PQ1 was prepared to provide water-soluble material for biological evaluation. Succinic acid alone does not show bioactivities. The interaction between the NH3+ group (under physiological conditions, N4'-amino function of PQ1 exists as protonated form) of PQ1 with the carboxylate ion (negatively charged) of Glu 146 of the Cx43 may be significant.

PQ1 protects R28 cells from ischemic apoptosis induced by cobalt chloride ($CoCl_2$)

Figure 20:
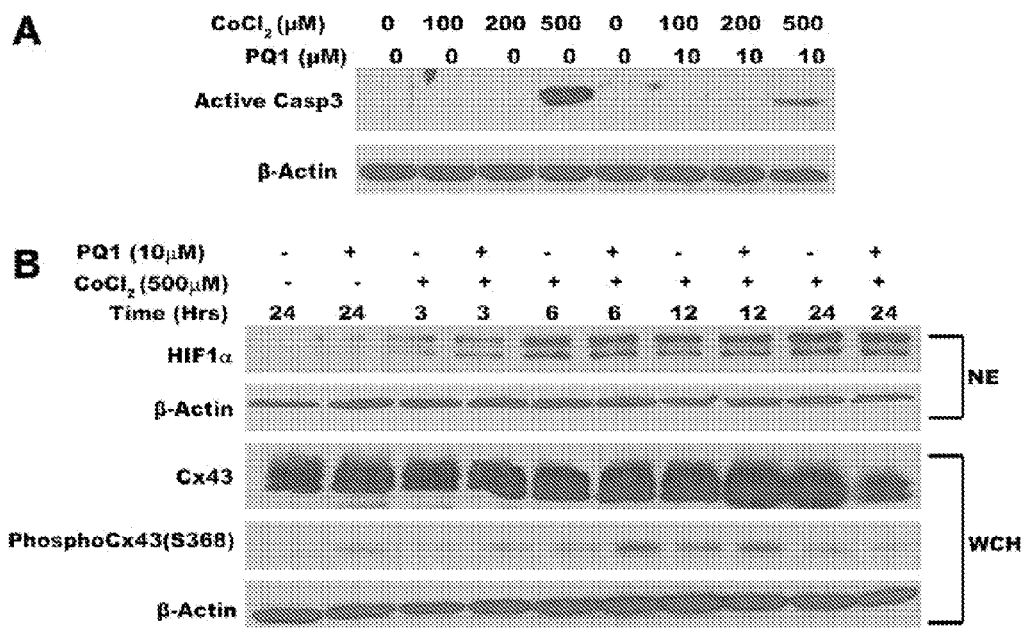
FIG. 20 shows Protection of PQ1 from $CoCl_2$-induced hypoxia in R28 cells. (A) About 70% confluent retinal R28 cells were treated with 100, 200 and 500 µM $CoCl_2$ for 24 h with or without the pre-treatment of PQ1 (10 µM, 40 min) in a cell culture chamber (5% $CO_2$, room air, 37° C.). Caspase-3 activation was determined by Western blotting in whole cell homogenates (WCH). (B) HIF1α stabilization was measured in the nuclear extracts (NE) after treatment with 500 µM $CoCl_2$ at different time intervals with or without the pretreatment of PQ1. $CoCl_2$ treatment stabilized HIF1α levels in the NE as early as after 3 h; PQ1 alone did not have any effect on HIF1α stabilization even after 24 h. Levels of Cx43 and phosphoCx43-Ser368 are measured in WCH. β-Actin is used as a loading control.

Next, it was determined whether PQ1 inhibition of gap junctions could prevent retinal neurosensory R28 cells from apoptosis using a chemical ($CoCl_2$)-induced ischemia system as our model. As shown in FIG. 20A, $CoCl_2$ incubation at 500 µM for 24 h induced activation of caspase-3. Pre-incubation of R28 cells with PQ1 at 10 µM for 40 min followed by co-incubation with $CoCl_2$ for additional 24 h blocked the activation of caspase-3 substantially. $CoCl_2$ at 500 µM caused stabilization of HIF1a in the nuclear extracts and this stabilization started as early as three hours after treatment (FIG. 20B). This confirmed induction of hypoxia. PQ1 alone did not cause activation or stabilization of caspase-3 or HIF1α, respectively. PQ1, $CoCl_2$ or a combination of both did not cause any change in the Cx43 gap junction protein levels or phosphorylation of Cx43 at residue ser368. Activation of Caspase-3 and stabilization of HIF1a indicates hypoxia-induced apoptosis in $CoCl_2$ treated cells. Pre-treatment with PQ1 was able to prevent the activation of Caspase-3 by $CoCl_2$. To confirm apoptosis, Annexin V-FITC/PI staining of cells was done. The early apoptotic stage is characterized by the cell membrane exposure of phosphatidylserine normally restricted to the inner cell membrane, which is recognized by Annexin V-FITC.

Figure 21:
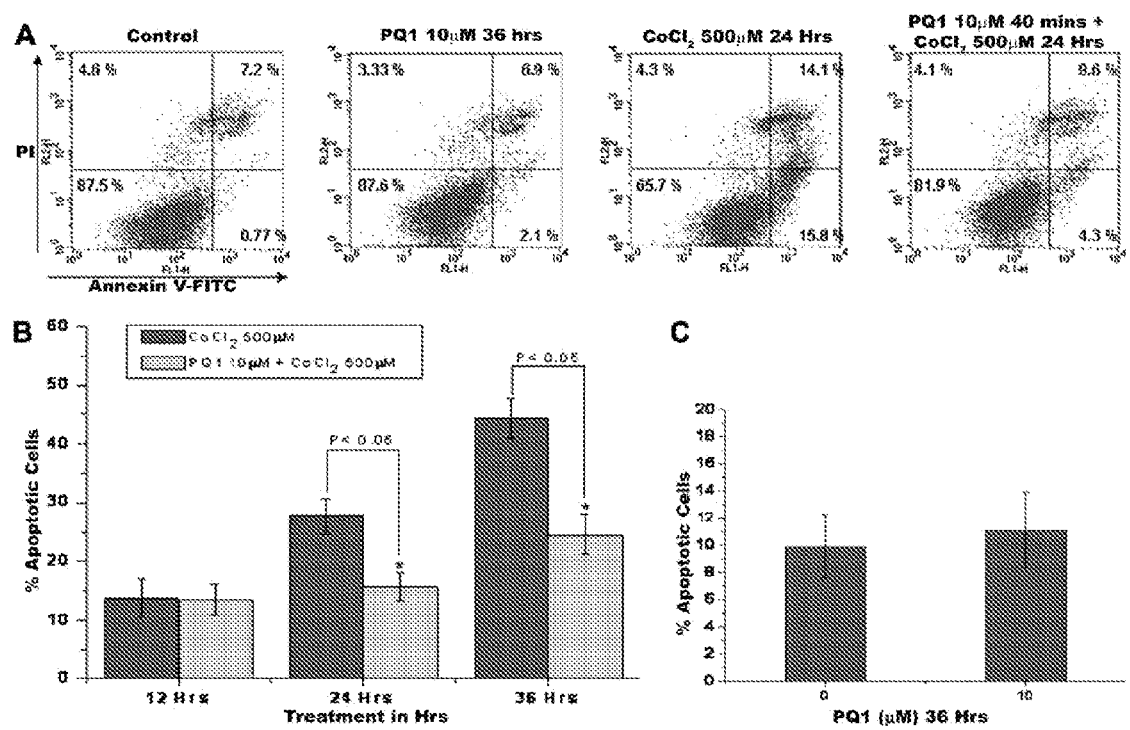
FIG. 21 shows apoptosis assay using the Annexin V-FITC Kit. (A) Representative flow cytometer images of R28 cells with different treatments of PQ1 and/or $CoCl_2$. The y-axis quantifies the number of cells stained with propidium iodine and the x-axis quantifies number of cells stained with Annexin V-FITC. (B,C) Histogram of % apoptotic cells after treatment with CoCl$_2$ and PQ1. The percentage of apoptotic cells represents cells that are Annexin V-FITC positive and both propidium iodide and Annexin V-FITC positive after different time periods.

The later phase of apoptosis is assessed by measuring the DNA labeling with the PI, an indicator of the cell membrane permeabilization. Once again, CoCl2 at 500 µM for 24 h was found to cause significant apoptosis (FIGS. 21A & B). Pre-treatment of R28 cells with 10 µM PQ1 for 40 min followed by incubation with CoCl$_2$ at 500 µM protected the cells significantly from undergoing apoptosis (FIG. 21). Treatment of cells only with 10 µM PQ1 did not cause any damage to the cells even after 36 h (FIG. 21C). These data show that inhibition of gap junctions by PQ1 protects cells from CoCl$_2$-induced ischemic apoptosis.

REFERENCES 1. van Riemsdijk, M. M.; Sturkenboom, M. C. J. M.; Ditters, J. M.; Ligthelm, R. J.; Overbosch, D.; Stricker, B. H. Ch. Atovaquone plus chloroguanide versus mefloquine for malaria prophylaxis: a focus on neuropsychiatric adverse events. Clin. Pharmacol. & Therapeutics, 2992, 72, 294-301.
2. Cruikshank, S. J.; Hopperstad, M.; Younger, M.; Connors, B. W.; Spray, D. C.; Srinivas, M. Potent block of Cx36 and Cx50 gap junction channels by mefloquine. PNAS 2004, 101, 12364-12369.
3. Veenstra, R. D.; Towards gap junction channel structure. Recent Res. Devel. Biophys. 2003, 2, 65-94.
4. LaMontagne, M. P.; Blumbergs, P.; Smith, D. C. Antimalarials. 16. Synthesis of 2-substituted analogs of 8-[(4-amino-1-methylbutyl)amino]-6-methoxy-4-methyl-5-[3-(trifluoromethyl)phenoxy]-quinoline as candidate antimalarials. J. Med. Chem. 1989, 32, 1728-1732.
5. LaMontagne, M. P.; 14. 5-(Aryloxy)-4-methylprimaquine analogues. A highly effective series of blood and tissue Schizonticidal agents. J. Med. Chem. 1982, 25, 1094-1097.
6. Steck, E. A. In "The Chemotherapy of Protozoan Diseases", Vol. III, U.S. Army Medical Research and Development Command, Washington, D.C., 1972, p 23-141.
7. Das, S.; Lauer, J.; Barnett, M.; Lin, D.; Akoev, V.; Battina, S.; Hua, D. H.; Takemoto, D. J. PKC☐ phosphorylates connexin 50 on serine-430. 2006 Association of Research in Visual and Opthalmology (ARVO) Annual Meeting. Apr. 30-May 4, 2006, Fort Lauderdale, Fla.
8. LaMontagne, M. P.; Markovac, A.; Khan, M. S. Antimalarials. 13. 5-Alkoxy analogues of 4-methylprimaquine. J. Med. Chem. 1982, 25, 964-968.
9. Lauer, W. M.; Rondestvedt, C.; Arnold, R. T.; Drake, N. L.; van Hook, J.; Tinker, J. Some derivatives of 8-aminoquinoline. J. Am. Chem. Soc. 1946, 48, 1546-1548.
10. Matayoshi, E. D., G. T. Wang, G. A. Krafft, and J. Erickson. Novel fluorogenic substrates for assaying retroviral proteases by resonance energy transfer. Science, 1990, 247, 954-8.
11. Luker, K. E., S. E. Francis, I. Y. Gluzman, and D. E. Goldberg. Kinetic analysis of plasmepsin I and II aspartic proteases of the *Plasmodium falciparum* digestive vacuole. Mol. Biochem. Parasitol. 1996, 79, 71-8.
12. Klenke, B.; Stewart, M.; Barrett, M. P.; Brun, R.; Gilbert, I. H. Synthesis and biological evaluation of s-triazine substituted polyamines as potential new anti-trypanosomal drugs. J. Med. Chem. 2001, 44, 3440-3452.
13. DeGraw, J. I.; Engstrom, J.; Ellis, M.; Johnson, H. L. Potential histidine decarboxylase inhibitors. 1. α- and β-Substituted histidine analogs. J. Med. Chem. 1977, 20, 1671-4.
14. Jones, Reuben G. Synthesis of some amines and amino acids containing the pyrazole nucleus. J. Am. Chem. Soc. 1949, 71, 3994-4000.

Am. J. Trop. Med. Hyg. 58(5), 1998, p. 645-649; Pharmacol. Ther. 79(1), 1998, p. 55-87; J. Med. Chem. 32, 1989, p. 1728-1732; U.S. Pat. Nos. 7,145,014, 4,980,360, 6,479,660, 4,617,394, 4,431,807, 6,376,511.

Acevedo P, Bertram J S. 1995. Liarozole potentiates the cancer chemopreventive activity of and the up-regulation of gap junctional communication and connexin43 expression by retinoic acid and beta-carotene in 10T1/2 cells. Carcinogenesis 16(9):2215-22.

Ammerpohl O, Thormeyer D, Khan Z, Appelskog I B, Gojkovic Z, Almqvist P M, Ekstrom T J. 2004. HDACi phenylbutyrate increases bystander killing of HSV-tk transfected glioma cells. Biochem Biophys Res Commun 324(1):8-14.

Bhimani R S, Troll W, Grunberger D, Frenkel K. 1993. Inhibition of oxidative stress in HeLa cells by chemopreventive agents. Cancer Res 53(19):4528-33.

Boyle R G, Travers, S. 2006. Hypoxia: targeting the tumor. Anti-cancer Agents in Med. Chem. (6):281-286.

Bruzzone R, White T W, Paul D L. 1996. Connections with connexins: the molecular basis of direct intercellular signaling. Eur J Biochem 238(1):1-27.

Clark P E, Hall M C, Borden L S, Jr., Miller A A, Hu J J, Lee W R, Stindt D, D'Agostino R, Jr., Lovato J, Harmon M and others. 2006. Phase I-II prospective dose-escalating trial of lycopene in patients with biochemical relapse of prostate cancer after definitive local therapy. Urology 67(6):1257-61.

Cnubben N H P, Wortelboer, H. M., van Zanden, J. J., Rietjens, V. M. C. M., van Bladeren, P. J. 2005. Metabolism of ATP-binding cassette drug transporter inhibitors: complicating factor for multidrug resistance. Expert Opinion on Drug Metabol. & Toxicol., (1):219-232.

Dubina M V, Iatckii N A, Popov D E, Vasil'ev S V, Krutovskikh V A. 2002. Connexin 43, but not connexin 32, is mutated at advanced stages of human sporadic colon cancer. Oncogene 21 (32):4992-6.

Eghbali B, Kessler J A, Reid L M, Roy C, Spray D C. 1991. Involvement of gap junctions in tumorigenesis: transfection of tumor cells with connexin 32 cDNA retards growth in vivo. Proc Natl Acad Sci USA 88(23):10701-5.

Fleishman S J, Unger V M, Ben-Tal N. 2006. Transmembrane protein structures without X-rays. Trends Biochem Sci 31(2):106-13.

Foote C I, Zhou L, Zhu X, Nicholson B J. 1998. The pattern of disulfide linkages in the extracellular loop regions of connexin 32 suggests a model for the docking interface of gap junctions. J Cell Biol 140(5):1187-97.

Goldberg G S, Martyn K D, Lau A F. 1994. A connexin 43 antisense vector reduces the ability of normal cells to inhibit the foci formation of transformed cells. Mol Carcinog 11(2):106-14.

Goodsell D S, Olson A J. 1990. Automated docking of substrates to proteins by simulated annealing. Proteins 8(3): 195-202.

Holder J W, Elmore E, Barrett J C. 1993. Gap junction function and cancer. Cancer Res 53(15):3475-85.

Huang R P, Hossain M Z, Huang R, Gano J, Fan Y, Boynton A L. 2001. Connexin 43 (cx43) enhances chemotherapy-induced apoptosis in human glioblastoma cells. Int J Cancer 92(1):130-8.

Jemal A, Siegel R, Ward E, Murray T, Xu J, Thun M J. 2007. Cancer statistics, 2007. CA Cancer J Clin 57(1):43-66.

Kawase M, Motohashi, N. 2003. New multidrug resistance reversal agents. Curr. Drug Targets (4):31-43.

LaMontagne M P, Blumbergs P, Strube R E. 1982a. Antimalarials. 14. 5-(aryloxy)-4-methylprimaquine analogues. A highly effective series of blood and tissue schizonticidal agents. J Med Chem 25(9):1094-7.

LaMontagne M P, Markovac A, Khan M S. 1982b. Antimalarials. 13. 5-Alkoxy analogues of 4-methylprimaquine. J Med Chem 25(8):964-8.

Lauer W M R, C.; Arnold, R. T.; Drake, N. L.; Hook, J. V.; Tinker, J. 1946. Some derivatives of 8-aminoquinoline. J. Am. Chem. Soc. (68):1546-1548.

Levitt M L, Koty, P. P. 1999. Tyrosine kinase inhibitors in preclinical development. Invest. New Drugs (17):213-226.

Livny O, Kaplan I, Reifen R, Polak-Charcon S, Madar Z, Schwartz B. 2002. Lycopene inhibits proliferation and enhances gap-junction communication of KB-1 human oral tumor cells. J Nutr 132(12):3754-9.

Loewenstein W R. 1979. Junctional intercellular communication and the control of growth. Biochim Biophys Acta 560(1):1-65.

Loewenstein W R. 1981. Junctional intercellular communication: the cell-to-cell membrane channel. Physiol Rev 61(4):829-913.

Loewenstein W R, Kanno Y. 1966. Intercellular communication and the control of tissue growth: lack of communication between cancer cells. Nature 209(5029):1248-9.

Makowski L, Caspar D L, Phillips W C, Goodenough D A. 1977. Gap junction structures. II. Analysis of the x-ray diffraction data. J Cell Biol 74(2):629-45.

Martin P E, Evans W H. 2004. Incorporation of connexins into plasma membranes and gap junctions. Cardiovasc Res 62(2):378-87.

Morris G M, Goodsell D S, Huey R, Olson A J. 1996. Distributed automated docking of flexible ligands to proteins: parallel applications of AutoDock 2.4. J Comput Aided Mol Des 10(4):293-304.

Morris G M, Goodsell, D. S., Halliday, R. S., Huey, R., Hart, W. E., Belew, R. K., Olson, A. J. 1998. Automated docking using Lamarckian genetic algorithm and an empirical binding free energy function. J. Comp. Chem. 19:1639-1662.

Musil L S, Le A C, VanSlyke J K, Roberts L M. 2000. Regulation of connexin degradation as a mechanism to increase gap junction assembly and function. J Biol Chem 275(33):25207-15.

Na H K, Wilson M R, Kang K S, Chang C C, Grunberger D, Trosko J E. 2000. Restoration of gap junctional intercellular communication by caffeic acid phenethyl ester (CAPE) in a ras-transformed rat liver epithelial cell line. Cancer Lett 157(1):31-8.

O'Byrne K J, Han C, Mitchell K, Lane D, Carmichael J, Harris A L, Talbot D C. 1998. Phase II study of liarozole in advanced non-small cell lung cancer. Eur J Cancer 34(9):1463-6.

Ruch R J. 1994. The role of gap junctional intercellular communication in neoplasia. Ann Clin Lab Sci 24(3):216-31.

Ruch R J, Madhukar B V, Trosko J E, Klaunig J E. 1993. Reversal of ras-induced inhibition of gap-junctional intercellular communication, transformation, and tumorigenesis by lovastatin. Mol Carcinog 7(1):50-9.

Saez C G, Velasquez L, Montoya M, Eugenin E, Alvarez M G. 2003. Increased gap junctional intercellular communication is directly related to the anti-tumor effect of all-trans-retinoic acid plus tamoxifen in a human mammary cancer cell line. J Cell Biochem 89(3):450-61.

Trosko J E, Chang C C. 2001. Mechanism of up-regulated gap junctional intercellular communication during chemoprevention and chemotherapy of cancer. Mutat Res 480-481:219-29.

Trosko J E, Chang C C, Madhukar B V, Klaunig J E. 1990. Chemical, oncogene and growth factor inhibition gap junctional intercellular communication: an integrative hypothesis of carcinogenesis. Pathobiology 58(5):265-78.

Unger V M, Kumar N M, Gilula N B, Yeager M. 1999. Three-dimensional structure of a recombinant gap junction membrane channel. Science 283(5405):1176-80.

Veenstra R D. 2003. gap junction channel structure. Recent Res. Devel. Biophys. 2:65-94.

Veyssier P, Bryskier, A. 2005. Dihydrofolate reductase inhibitors, nitroheterocycles (furans) and 8-hydroxyquinolines. Internal Medicine, Hospital de Compiegne, Bryskier, A. Ed., Compiegne, Fr. P 941-963.

Wei N, Mi M T, Zhou Y. 2007. Influences of lovastatin on membrane ion flow and intracellular signaling in breast cancer cells. Cell Mol Biol Lett 12(1):1-15.

Wiesner J, Ortmann, R., Jomaa, H., Schlitzer, M. 2003. New antimalarial drugs. Angew. Chem. Int. Ed. (42):5274-5293.

Wilgenbus K K, Kirkpatrick C J, Knuechel R, Willecke K, Traub O. 1992. Expression of Cx26, Cx32 and Cx43 gap junction proteins in normal and neoplastic human tissues. Int J Cancer 51 (4):522-9.

Yamasaki H, Naus C C. 1996. Role of connexin genes in growth control. Carcinogenesis 17(6):1199-213.

Zhang Z Q, Lin Z X, Lu Y Y. 1994. Studies on the reduction of malignant phenotypes in a highly metastatic human lung carcinoma—correlated changes of intercellular communication, cytoskeletons, oncogenes and antioncogene. Cancer Research 16(2):88-92.

Zhu D, Kidder G M, Caveney S, Naus C C. 1992. Growth retardation in glioma cells cocultured with cells overexpressing a gap junction protein. Proc Natl Acad Sci USA 89(21):10218-21.

[1] N. N. Osborne, R. J. Casson, J. P. Wood, G. Chidlow, M. Graham, J. Melena, Retinal ischemia: mechanisms of damage and potential therapeutic strategies, Prog. Retin. Eye Res. 23 (2004) 91-147.

[2] W. Kamphuis, F. Dijk, A. A. Bergen, Ischemic preconditioning alters the pattern of gene expression changes in response to full retinal ischemia, Mol. Vis. 13 (2007) 1892-1901.

[3] R. R. Leker, E. Shohami, Cerebral ischemia and trauma-different etiologies yet similar mechanisms: neuroprotective opportunities, Brain Res. Rev. 39 (2002) 55-73.

[4] R. Farahani, M. H. Pina-Benabou, A. Kyrozis, A. Siddiq, P. C. Barradas, F. C. Chiu, L. A. Cavalcante, J. C. Lai, P. K. Stanton, R. Rozental, Alterations in metabolism and gap junction expression may determine the role of astrocytes as "good samaritans" or executioners, Glia 50 (2005) 351-361.

[5] R. J. Thompson, N. Zhou, B. A. MacVicar, Ischemia opens neuronal gap junction hemichannels, Science 312 (2006) 924-927.

[6] K. Cusato, A. Bosco, R. Rozental, C. A. Guimaraes, B. E. Reese, R. Linden, D. C. Spray, Gap junctions mediate bystander cell death in developing retina, J. Neurosci. 23 (2003) 6413-6422.

[7] J. H. Lin, H. Weigel, M. L. Cotrina, S. Liu, E. Bueno, A. J. Hansen, T. W. Hansen, S. Goldman, M. Nedergaard, Gap-junction-mediated propagation and amplification of cell injury, Nat. Neurosci. 1 (1998) 494-500.

[8] J. Neijssen, C. Herberts, J. W. Drijfhout, E. Reits, L. Janssen, J. Neefjes, Cross-presentation by intercellular peptide transfer through gap junctions, Nature 434 (2005) 83-88.

[9] B. N. Giepmans, Gap junctions and connexin-interacting proteins, Cardiovasc. Res. 62 (2) (2004) 233-245.

[10] J. Velaquez, M. Frantseva, C. Naus, Gap junctions and neuronal injury: Protectants or executioners, Neuroscientist 9 (2003) 5-9.

[11] J. Contreras, H. Sanchez, L. Veliz, F. Bukauskas, M. Bennett, J. Saez, Role of connexin-based gap junctional channels and hemichannels in ischemia-induced cell death in nervous tissue, Brain Res. Rev. 47 (2004) 290-303.

[12] D. J. Rossi, J. D. Brady, C. Mohr, Astrocyte metabolism and signaling during brain ischemia, Nat. Neurosci. 10 (2007) 1377-1386.

[13] M. Singh, S. I. Savitz, R. Hoque, G. Gupta, S. Roth, P. S. Rosenbaum, D. M. Rosenbaum, Cell-specific caspase expression by different neuronal phenotypes in transient retinal ischemia, J. Neurochem. 77 (2001) 466-475.

[14] D. Lin, D. J. Takemoto, Protection from ataxia-linked apoptosis by gap junction inhibitors, Biochem. Biophys. Res. Commun. 362 (4) (2007) 982-987.

[15] M. H. de Pina-Benabou, V. Szostak, A. Kyrozis, D. Rempe, D. Uziel, M. Urban-Maldonado, S. Benabou, D. C. Spray, H. J. Federoff, P. K. Stanton, R. Rozental, Blockade of gap junctions in vivo provides neuroprotection after perinatal global ischemia, Stroke 36 (2005) 2232-2237.

[16] M. Guo, L.-P. Song, Y. Jiang, W. Liu, Y. Yu, G.-Q. Chen, Hypoxia-mimetic agents desferrioxamine and cobalt chloride induce leukemic cell apoptosis through different hypoxia-inducible factor-1 a independent mechanisms, Apoptosis 11 (2006) 67-77.

[17] A. Haraa, M. Niwab, H. Aokie, M. Kumadad, T. Kunisadae, T. Oyamaa, T. Yamamotod, O. Kozawab, H. Moria, A new model of retinal photoreceptor cell degeneration induced by a chemical hypoxia-mimicking agent, cobalt chloride, Brain Res. 1109 (2006) 192-200.

[18] M. Srinivas, J. Kronengold, F. F. Bukauskas, T. A. Bargiello, V. K. Verselis, Correlative studies of gating in Cx46 and Cx50 hemichannels and gap junction channels, Biophys. J. 88 (3) (2005) 1725-1739.

[19] S. J. Cruikshank, M. Hopperstad, M. Younger, B. W. Connors, D. C. Spray, M. Srinivas, Potent block of Cx36 and Cx50 gap junction channels by mefloquine, Proc. Natl. Acad. Sci. USA 101 (33) (2004) 12364-12369.

[20] D. R. Veenstra, Gap junction channel structure, Recent Res. Devel. Biophys. 2 (2003) 65-94.

[21] S. N. Zucker, B. J. Nicholson, Mutagenic approaches to modifying gap junction phenotype, Curr. Drug Targets 3 (2002) 441-453.

[22] S. D. Goodsell, J. A. Olson, Automated docking of substrates to proteins by simulated annealing, Proteins 8 (1990) 95-202.

[23] G. M. Morris, D. S. Goodsell, R. Huey, A. J. Olson, Distributed automated docking of flexible ligands to proteins: parallel applications of AutoDock 2.4, J. Comput. Aided Mol. Des. 10 (4) (1996) 293-304.

[24] G. M. Morris, D. S. Goodsell, R. S. Halliday, R. Huey, W. E. Hart, R. K. Belew, A. J. Olson Automated docking using a Lamarckian genetic algorithm and an empirical binding free energy function, J. Comp. Chem. 19 (1998) 1639-1662.

[25] M. P. LaMontagne, A. Markovac, M. S. Khan, Antimalarials. 13. 5-Alkoxy analogues of 4-methylprimaquine, J. Med. Chem. 25 (8) (1982) 964-968.

[26] M. P. LaMontagne, P. Blumbergs, R. E. Strube, Antimalarials. 14. 5-(aryloxy)-4-methylprimaquine analogues. A highly effective series of blood and tissue schizonticidal agents, J. Med. Chem. 25 (9) (1982) 1094-1097.

[27] W. M. Lauer, C. Rondestvedt, R. T. Arnold, N. L. Drake, J. V. Hook, J. Tinker, Some derivatives of 8-aminoquinoline, J. Am. Chem. Soc. 68 (1946) 1546-1548.

[28] D. Lin, D. J. Takemoto, Oxidative activation of protein kinase Cgamma through the C1 domain. Effects on gap junctions, J. Biol. Chem. 280 (2005) 13682-13693.

[29] L. R. Aminova, J. C. Chavez, J. Lee, H. Ryu, A. Kung, J. C. LaManna, R. R. Ratan, Prosurvival and prodeath effects of hypoxia-inducible factor-1 (stabilization in a murine hippocampal cell line, J. Biol. Chem. 280 (5) (2005) 3996-4003.

[30] G. L. Wang, G. L. semenza, Purification and characterization of hypoxia-inducible factor 1, J. Biol. Chem. 270 (3) (1995) 1230-1237.

[31] A. Shi, T. Nguyen, S. Battina, S. Rana, D. J. Takemoto, P. Chiang, D. H. Hua, Synthesis and anti-breast cancer activities of substituted quinolines, Bioorg. Med. Chem. Lett. 18 (2008) 3364-3368.

All references throughout this specification, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, and synthetic methods other than those specifically exemplified can be employed in the practice of the invention without resort to undue experimentation. All art-known functional equivalents, of any such methods, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention.

One skilled in the art readily appreciates that the present invention is well adapted to carry out the objects and obtain the ends and advantages mentioned, as well as those inherent in the present invention. The methods, components, materials and dimensions described herein as currently representative of preferred embodiments are provided as examples and are not intended as limitations on the scope of the invention. Changes therein and other uses which are encompassed within the spirit of the invention will occur to those skilled in the art, are included within the scope of the claims. Although the description herein contains certain specific information and examples, these should not be construed as limiting the scope of the invention, but as merely providing illustrations of some of the embodiments of the invention. Thus, additional embodiments are within the scope of the invention and within the claims.

The exact formulation, route of administration and dosage can be chosen by the individual physician in view of the patient's condition (see e.g. Fingl et. al., in The Pharmacological Basis of Therapeutics, 1975, Ch. 1 p. 1). It should be noted that the attending physician would know how to and when to terminate, interrupt, or adjust administration due to toxicity, or to organ dysfunctions, or to other undesired effects. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

We claim:
1. A compound having the following formula:

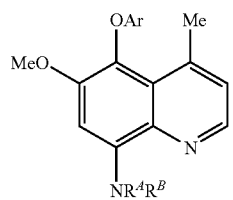

where Ar is o-, m- or p-$C_6H_4CF_3$;
$R^A$ and $R^B$ are independently selected from the group consisting of: hydrogen, —$(CH_2)_n$—$(X)_m$—Y, where n is an integer from 0-6; m is an integer from 0-2; X is independently —O—, —C(=O)—, —C(=NH)—, —S—, —S(=O)—, —$SO_2$—; and Y is selected from the group consisting of: hydrogen, C1-C6 alkyl groups and nitrogen containing groups comprising —$NH_2$; —$NO_2$; —CN; phthalimide; imidazole; pyrazole; pyridine; pyrimidine; pyrazine; and pyridazine, provided that $R^A$ and $R^B$ are not both hydrogen.

2. A compound having the formula:

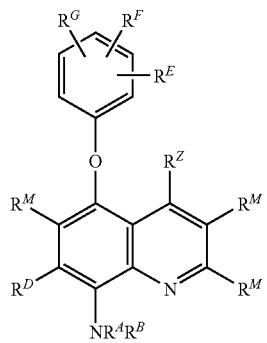

where $R^Z$, $R^M$ and $R^D$ are independently selected from the group consisting of:
hydrogen, halogen, aldehyde, ketone, alcohol, optionally substituted C1-C6 straight chain or branched alkyl or alkoxy, nitro, amine, alkylsulfanyl, alkylsulfinyl, alkylsulfonyl, arylsulfanyl, arylsulfinyl, and arylsulfonyl, where the optional substituents are independently halogen, nitro, amine, alkylsulfanyl, alkylsulfinyl, alkylsulfonyl, arylsulfanyl, arylsulfinyl, and arylsulfonyl;
$R^E$ and $R^F$ are hydrogen, $R^G$ is o-, p-, or m-$CF_3$;
$R^A$ and $R^B$ are independently selected from the group consisting of: hydrogen, —$(CH_2)_n$—$(X)_m$—Y, where n is an integer from 0-3; m is an integer from 0-2; X is independently —O—, —C(=O)—, —C(=NH)—, —S—, —S(=O)—, —$SO_2$—; and Y is selected from the group consisting of: hydrogen, C1-C3 straight chain or branched alkyl or alkoxy, and nitrogen containing groups including —$NH_2$, —$NO_2$, —CN, phthalimide imidazole, pyrazole, pyridine, pyrimidine, pyrazine, and pyridazine and pharmaceutically acceptable salts thereof, provided that $R^A$ and $R^B$ are not both hydrogen.

3. The compound of claim 2, wherein $R^M$ is OMe.

4. The compound of claim 1, wherein $R^A$ is hydrogen and $R^B$ is —$(CH_2)_n$—$(X)_m$—Y, where m is 0, and Y is selected from the group consisting of —$NH_2$; —$NO_2$; —CN; phthalimide; imidazole; and pyrazole.

5. The compound of claim 4, wherein $R^A$ is hydrogen and $R^B$ is —$(CH_2)_n$—$(X)_m$—Y, where m is 0, and Y is a nitrogen-containing group.

6. The compound of claim 1, having formula:

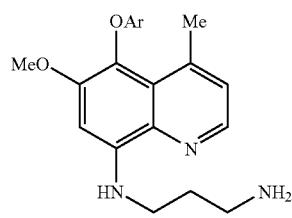

where Ar is o-, p-, or m-$C_6H_4CF_3$.

7. The compound of claim 1, having formula:

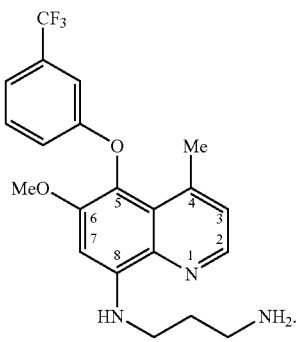 [SMILES: COc1cc(NCCCN)c2nccc(C)c2c1Oc1cccc(C(F)(F)F)c1]

8. The compound of claim 1, wherein Ar is o-, p-, or m-$C_6H_4CF_3$; $R^A$ is hydrogen and $R^B$ is —$(CH_2)_n$—$(X)_m$—Y, where n is 1; m is 0; and Y is imidazole.

9. A compound of claim 2 which affects gap junction activity.

10. A pharmaceutical composition comprising the compound of claim 1 and a pharmaceutically acceptable carrier.

11. A method for treating a gap junction disorder, wherein the disorder is selected from ischemia, cancer, or parasitic infections, comprising administering an effective amount of the compound of claim 2.

12. A method for treating a gap junction disorder, wherein the disorder is selected from ischemia, cancer, or parasitic infections, comprising administering an effective amount of the compound of claim 1 to a patient.

13. The method of claim 12, wherein $R^A$ is hydrogen and $R^B$ is —$(CH_2)_n$—$(X)_m$—Y, where m is 0, and Y is selected from the group consisting of —$NH_2$; —$NR_2$, where R is C1-C6 alkyl; —$NO_2$; —CN; phthalimide; imidazole; and pyrazole.

14. The method of claim 12, where the gap junction disorder is cancer and the compound is

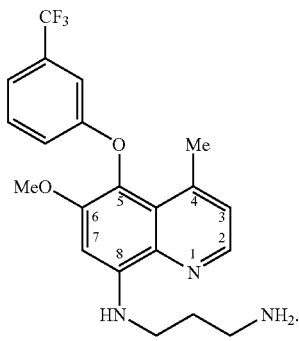 [SMILES: COc1cc(NCCCN)c2nccc(C)c2c1Oc1cccc(C(F)(F)F)c1]

15. The method of claim 12, wherein $R^A$ is hydrogen and $R^B$ is —$(CH_2)_n$—$(X)_m$—Y, where m is 0, and Y is selected from the group consisting of —$NH_2$; —$NO_2$; —CN; phthalimide; imidazole; and pyrazole.

16. The method of claim 12, wherein the compound of claim 1 has the formula:

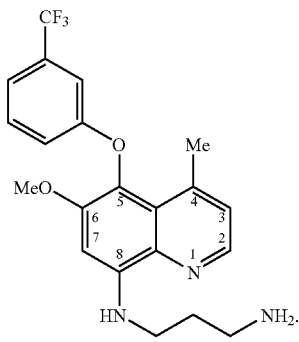 [SMILES: COc1cc(NCCCN)c2nccc(C)c2c1Oc1cccc(C(F)(F)F)c1]

17. The method of claim 12, wherein Ar is m-$C_6H_4CF_3$; $R^A$ is hydrogen and $R^B$ is —$(CH_2)_n$—$(X)_m$—Y, where n is 1; m is 0; and Y is imidazole.

* * * * *